(12) United States Patent
Erver et al.

(10) Patent No.: US 11,505,544 B2
(45) Date of Patent: *Nov. 22, 2022

(54) PROCESS FOR PREPARING ANTIHELMINTIC 4-AMINO-QUINOLINE-3-CARBOXAMIDE DERIVATIVES

(71) Applicant: Bayer Animal Health GMBH, Leverkusen (DE)

(72) Inventors: Florian Erver, Wiesbaden (DE); Frank Memmel, Guntersblum (DE); Thomas Himmler, Odenthal (DE); Andreas Karl Steib, Wuppertal (DE); Marc Nowakowski, Wuppertal (DE)

(73) Assignee: Bayer Animal Health GMBH, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/772,680

(22) PCT Filed: Dec. 14, 2018

(86) PCT No.: PCT/EP2018/084964
§ 371 (c)(1),
(2) Date: Jun. 12, 2020

(87) PCT Pub. No.: WO2019/115768
PCT Pub. Date: Jun. 20, 2019

(65) Prior Publication Data
US 2020/0308153 A1    Oct. 1, 2020

(30) Foreign Application Priority Data
Dec. 15, 2017 (EP) .................... 17207586

(51) Int. Cl.
*C07D 405/12* (2006.01)
*B01J 23/44* (2006.01)
*C07D 215/56* (2006.01)

(52) U.S. Cl.
CPC ......... *C07D 405/12* (2013.01); *B01J 23/44* (2013.01); *C07D 215/56* (2013.01)

(58) Field of Classification Search
CPC .................................................. C07D 405/12
USPC ...................................................... 514/336
See application file for complete search history.

(56) References Cited

U.S. PATENT DOCUMENTS

| 6,093,732 | A | 7/2000 | Tucker |
| 10,889,573 | B2 * | 1/2021 | Hubsch ............ C07D 405/14 |
| 2003/0144507 | A1 | 7/2003 | Haneda |
| 2013/0210844 | A1 | 8/2013 | Gharat |

FOREIGN PATENT DOCUMENTS

| EP | 1258252 B1 | 4/2010 |
| JP | 2008214323 A | 9/2008 |
| WO | WO2013118071 A1 | 8/2013 |
| WO | WO2015078800 A1 | 6/2015 |
| WO | WO2017103851 A1 | 6/2017 |
| WO | WO2018087036 A1 | 5/2018 |

OTHER PUBLICATIONS

Porras, J. Org. Chem. 2016, 81, 11548-11555.*
Dorow, R. L. et al. (2006) "Development of an Efficient Synthesis of the Pyrrolquinolone PHA-529311," Organic Process Research & Development, 10(3):493-499.
Hajimahdi, Z. et al. (2016) "Novel quinolone-3-carboxylic acid derivatives as anti-HIV-1 agents: design, synthesis, and biological activities," Med Chem Res 25:1861-1876.
International Search Report and Written Opinion dated Jan. 28, 2019 for International Application No. PCT/EP2018/084964 filed Dec. 14, 2018, 16 pages.
Ohnmacht JR., C.J. et al. (1971). "Antimalarials. 5. α-Dibutylaminomethyl- and α-(2-Piperidyl)-3-quinolinemethanols," Journal of Medicinal Chemistry 14: 17-24.
Price C., et al. (Jul. 1946) "The Synthesis of 4-Hydroxyquinolines. I. Through Ethoxymethylenemalonic Ester," J Am Chem Soc 68:1204-1208.
Srivastava, S. et al. (2000) "Quinolones: Novel Probes in Antifilarial Chemotheraphy," J. Med. Chem., 43:2275-2279.
Todorov, A. et al. (2017) "Photoreductive Removal of O-Benzyl Groups from Oxyarene N-Heterocycles Assisted by O-Pyridine-pyridone Tautomerism," J. Org. Chem., 82:13756-13767.
White, T. et al. (2014) "How to Convert a Walk-in Hood into a Manufacturing Facility: Demonstration of a Continuous, High-Temperature Cyclization to Process Solids in Flow," Org. Process Res. Dev., 18:1482-1491.
Zask, A. et al. (2003). "Synthesis and SAR of Bicyclic Heteroaryl Hydroxamic Acid MMP and TACE Inhibitors," Bioorganic & Medicinal Chemistry Letters 13: 1487-1490.

(Continued)

*Primary Examiner* — Nizal S Chandrakumar
(74) *Attorney, Agent, or Firm* — McBee Moore & Vanik IP, LLC; Susan McBee

(57) ABSTRACT

The present invention relates to a new process for preparing quinoline compounds of the general formula (II): in which Q, A, R4, $R^3$ and $R^{3'}$, are as defined herein, as well as to the intermediate compounds of said new process.

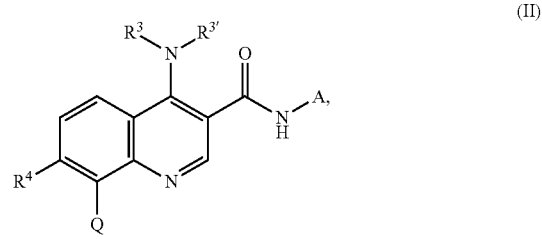

12 Claims, No Drawings

(56) References Cited

OTHER PUBLICATIONS

Aly et. al., "Novel quinoline-3-carboxamides (Part 2): Design, optimization and synthesis of quinoline based scaffold as EGFR inhibitors with potent anticancer activity", Bioorganic Chemistry, 2017, pp. 368-392, vol. No. 75.
Liu et al,."4-Oxo-1,4-dihydro-quinoline-3-carboxamides as BACE-1 inhibitors: Synthesis, biological evaluation and docking studies",European Journal of Medicinal Chemistry, 2014, pp. 413-421, vol. No. 79.
Li et al., "Quinoline-3-carboxamide Derivatives as Potential Cholesteryl Ester Transfer Protein Inhibitors", Molecules, 2012, pp. 5497-5507, vol. No. 17.

* cited by examiner

PROCESS FOR PREPARING ANTIHELMINTIC 4-AMINO-QUINOLINE-3-CARBOXAMIDE DERIVATIVES

CROSS REFERENCE TO RELATED APPLICATIONS

This application is a national stage application under 35 U.S.C. § 371 of International Application No. PCT/EP2018/084964, filed internationally on Dec. 14, 2018 which claims benefit of European Application No. 17207586.3, filed Dec. 15, 2017.

The present invention relates to a new process for preparing quinoline compounds of the general formula (II):

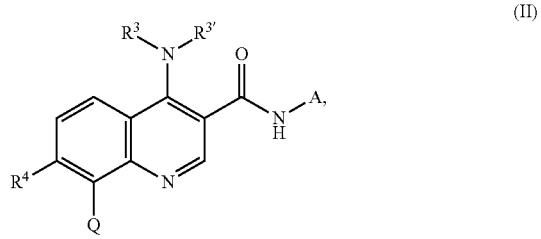

(II)

in which $R^3$ and $R^{3'}$ may have the meaning of hydrogen, $C_1$-$C_3$-alkyl, or together with the nitrogen to which they are bonded form a morpholinyl-ring, $R^4$ may have the meaning of hydrogen or halogen, Q may have the meaning of phenyl which may be substituted with 1 to 5 substituents $Z^1$ to $Z^5$, which are selected from hydrogen, halogen, $C_1$-$C_4$-alkyl and $C_1$-$C_4$-halogenoalkyl having 1-5 halogen atoms, and A is a group selected from

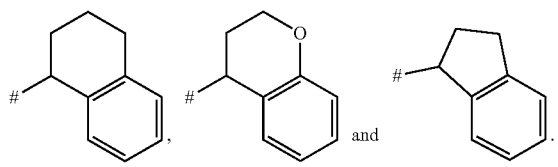

The present invention further relates to the intermediate compounds of the new process of the present invention.

BACKGROUND

The present invention relates to a new and improved process for preparing quinoline compounds of the general formula (II) supra, such as in particular of quinoline compounds according to the formula (III):

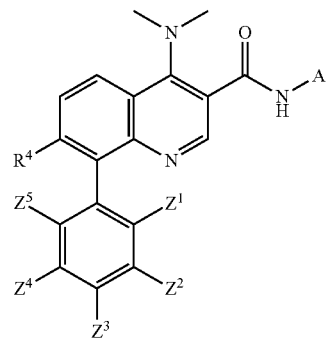

(III)

in which A, $R^4$ and $Z^1$ to $Z^5$ are as defined herein, as well as to the intermediate compounds of said new process.

The compounds of the general formula (II) and (III), which are obtainable by the process of the present invention demonstrate a valuable pharmacological spectrum of action and have been found to effectively interact with Slo-1 and can therefore be utilized to control, treat and/or prevent helminth infections, in particular gastro-intestinal and extra-intestinal helminth infections.

Certain quinoline carboxamides are described in JP2008-214323A as agents suitable for treatment and/or prevention of skin diseases, like acne vulgaris, dermatitis or the like.

The WO2017103851 discloses quinoline-3-carboxamides as H-PGDS inhibitors, useful for treating atherosclerosis, psoriasis, sinusitis, and duchenne muscular dystrophy.

Further, the unpublished international application PCT/EP2017/078319 discloses quinoline derivatives covered by the general formula (II) and (III) of the present invention and a method for obtaining such compounds, comprising 6 process steps. With the 6-steps-process described therein a total yield of less than 37% can be achieved.

It was thus the object of the present invention to provide an improved process for preparing the compounds according to formula (II) and (III) as described herein. The improved process should in particular provide an increased space-time yield and thus be particularly suitable to allow the preparation of higher yields in shorter time and to apply optimised process conditions, which are in particular readily scalable, cost-effective, environmentally friendly and capable of consistently yielding highly pure compounds.

This object has been solved by providing the new process of the present invention, comprising 4 process steps with a dehydroxyamination step, a Suzuki coupling step, a saponification step and a further amide coupling step. The new process may further comprise a prior cyclocondensation step using Eaton's reagent for preparing the starting compounds (I) of the present invention.

The prior art describes dehydroxyamination e.g. in Bioorg. Med. Chem. Lett. 2003, p 1487-1490 or in WO 2013/118071 A1 and the corresponding US 2013/210844.

A cyclocondensation by using a thermal process and Eaton's reagent has been described in J. Am. Chem. Soc. 1946, p 1204-1208, Org. Proc. Res. Dev. 2006, p 493-499, Org. Proc. Res. Dev. 2014, p 1482-1491 or from EP1258252 and US2003/0144507.

In particular in view of the unpublished international application PCT/EP2017/078319 was possible with the new process of the present invention to increase the yield of the coupling step (Step B-d) from 66% to 90% by replacing the coupling agent HATU ([Bis(dimethylamino)methylene]-1H-1,2,3-triazolo[4,5-b]pyridinium 3-oxid hexafluorophosphate), as used in the unpublished international application PCT/EP2017/078319. The improved dehydroxyamination step (Step B-a) of the present invention provides a significant reduction of the reaction time from 27 hours to 6 hours with essentially the same yield, by providing a new telescoped dehydroxyamination, wherein the so far occurring additional process step of dechloroamination can be telescoped in a one-pot reaction, thus preventing isolation of the unstable chloro-intermediate and thereby increasing the space-time yield. In addition, it was possible to further increase the space-time yield by carrying out a prior cyclo-condensation step (Step A) under improved chemical activation instead of thermal activation, thereby achieving an increase of the yield of the starting compound (I) from 68% to 90%.

As mentioned above, compared to the 6-steps-process as described in the unpublished international application PCT/EP2017/078319, it was possible to increase the overall yield in the process for preparing compounds according to formula (II) or (III) from about 37% to more than 59% and at the same time reduce the the amount of synthesis steps and the overall time of the process, leading to a significant improvement of the space-time yield.

DESCRIPTION OF THE INVENTION

In accordance with a first aspect, the present invention relates to a process for preparing a compound according to the formula (II) supra from a compound according to the formula (I):

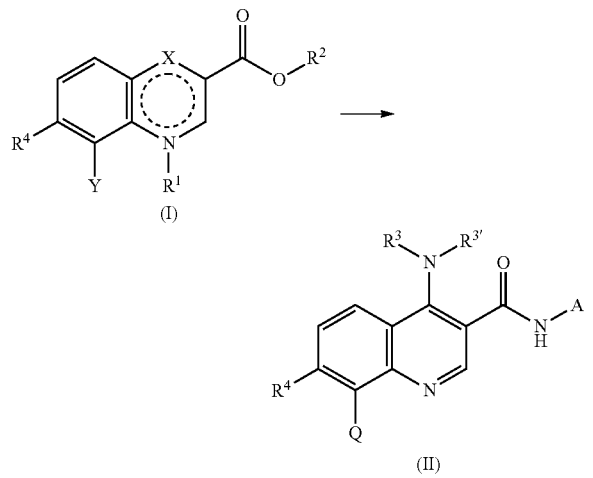

wherein
Y has the meaning of halogen or Q;
X has the meaning of C=O, C—OH or C—NR$^3$R$^{3'}$;

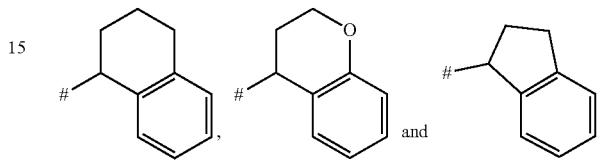

indicates an aromatic ring system or in the case that X is C=O valid double bonds in the ring system;
R$^1$ is absent in the case that X is C—OH or C—NR$^3$R$^{3'}$ or a hydrogen atom in the case that X is C=O;
R$^2$ has the meaning of hydrogen or C$_1$-C$_3$-alkyl;
R$^3$ and R$^{3'}$ independently have the meaning of hydrogen or C$_1$-C$_3$-alkyl, or R$^3$ and R$^{3'}$ together with the nitrogen to which they are bonded form a morpholinyl-ring
R$^4$ has the meaning of hydrogen or halogen;
Q has the meaning of phenyl, substituted with 1 to 5 substituents Z$^1$ to Z$^5$, wherein
Z$^1$ to Z$^5$ may independently be selected from hydrogen, halogen, C$_1$-C$_4$-alkyl, and C$_1$-C$_4$-halogenoalkyl having 1-5 halogen atoms; and
A is a group selected from

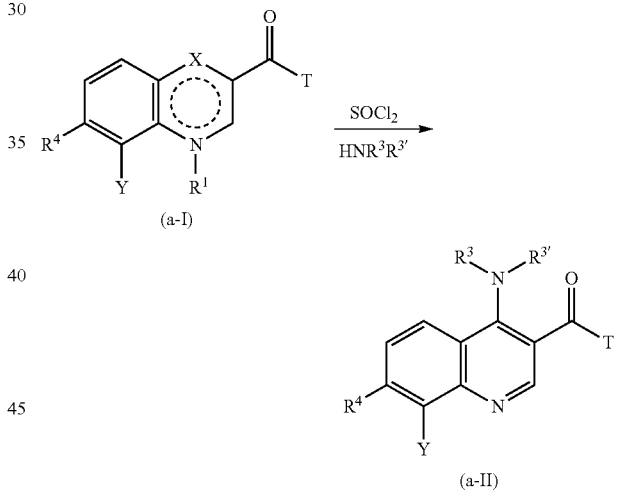

wherein in the process the groups Q, NR$^3$R$^{3'}$ and NH-A in formula (II) are obtained by reaction of the groups R$^2$, X and Y in formula (I) by the steps B-a, B-b, B-c and B-d, which can be carried out in any order, provided that Step B-d is not carried out prior to Step B-c:

Step B-a:

wherein T indicates a group —O—R$^2$ or —NH-A, with R$^2$ being hydrogen or C$_1$-C$_3$-alkyl; and wherein X is C=O and R$^1$ is hydrogen or X is C—OH and R$^1$ is absent, corresponding to the formulae (a-I-a) and (a-I-b):

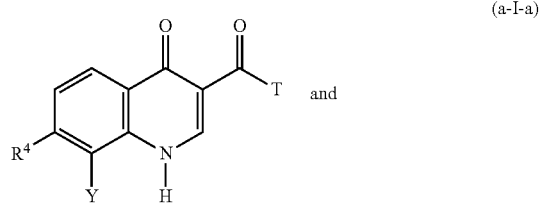

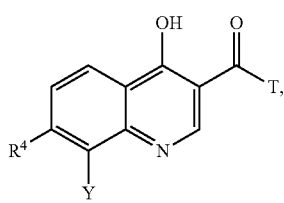

(a-I-b)

and wherein said process Step B-a is carried out using thionyl chloride (SOCl₂);

Step B-b:

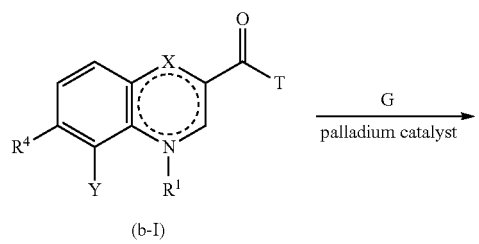

(b-I)

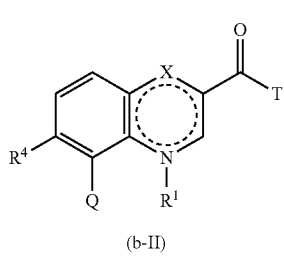

(b-II)

wherein Y is halogen, T indicates a group —O—R² or —NH-A, with R² being hydrogen or $C_1$-$C_3$-alkyl, and G indicates a boron compound suitable for carrying out a Suzuki-reaction, which may be defined as follows:

G represents a boron compound of the general formula (Q)$_n$B(OH)$_{3-n}$ with n=0, 1, 2, or 3 or

G represents a boron compound of the general formula (Q)$_4$B⁻M⁺ with

M=lithium, sodium, or potassium, or

G represents a boron compound of the general formula

QBF$_3^-$M⁺ with

M=lithium, sodium, or potassium, or

G represents a boron compound of the general formula

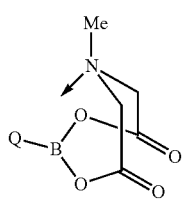

Step B-c:

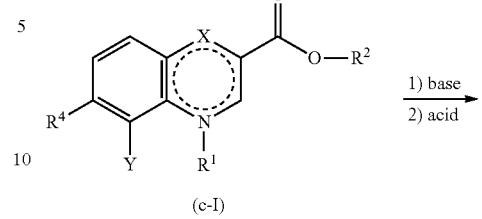

(c-I)

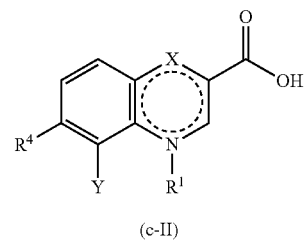

(c-II)

wherein R² is $C_1$-$C_3$-alkyl; wherein base corresponds to any alkali metal hydroxide and alkaline earth metal hydroxide, as well as any alkali metal carbonate and alkaline earth metal carbonate. Acid corresponds to any mineral acid.

Step B-d:

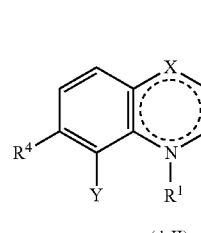

(d-I)

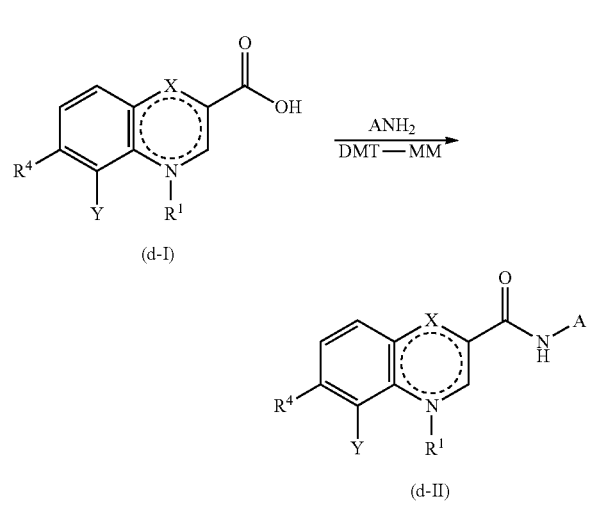

(d-II)

wherein said process Step B-d is carried out by using 4-(4,6-dimethoxy-1,3,5-triazin-2-yl)-4-methyl-morpholinium chloride (DMT-MM) as the coupling agent;

and wherein in the reaction steps B-a to B-d the remaining substituents have the meaning corresponding to the respective process stage. This means, that depending on the respective order of the process steps B-a, B-b, B-c and B-d, in particular the substituents Y, X, T or R² of the respective starting compounds as defined supra have the meaning, resulting from the respective prior reaction step.

As mentioned above, in the process of the present invention, in principle the reaction steps B-a, B-b, B-c and B-d can be carried out in any order, however, provided that Step B-d is not carried out prior to Step B-c.

In accordance with a second aspect of the present invention the process as defined supra may further comprise the previous Step A for preparing the compound according to the formula (I):

Step A:

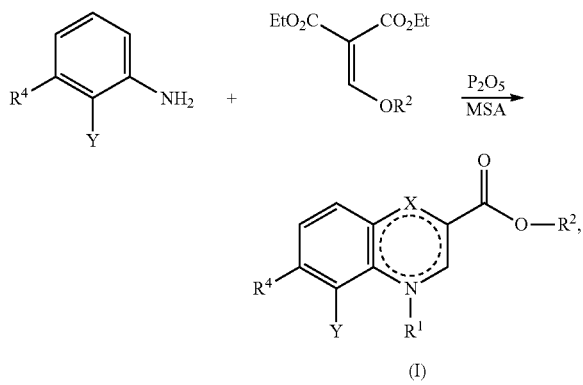

wherein Y, $R^4$, $R^1$ and $R^2$ have the meaning as defined supra, and
wherein said process Step A is carried out using $P_2O_5$ in an absolute amount of >1 equivalents $P_2O_5$ and in an amount of 15 to 25 wt.-% relative to the methane sulfonic acid (MSA).

Description of the Process Steps

Process Step A:

In the prior process Step A of the second aspect of the present invention an aniline is condensed with a diethyl 2-($R^2$-oxymethylene)propanedioate compound in the presence of $P_2O_5$ and methanesulfonic acid (MSA). It surprisingly turned out, that the chemoselectivity of said reaction is dependent on the absolute amount of $P_2O_5$ and on the amount relative to MSA.

An absolute amount of $\geq 1$ equivalents, preferably >1 equivalents, more preferably between 1.5 and 3.5 equivalents, preferably between 2.0 and 3.0 equivalents, more preferably about 2.5 equivalents $P_2O_5$ is used in process Step A of the present invention to achieve increased yields, in particular yields up to 90%.

Further, in the process Step A the amount of $P_2O_5$ relative to the amount of MSA is 7.0 to 23.0 wt. %, preferably 15.0 to 23.0 wt.-%, more preferably about 23.0 wt. %.

It turned out that surprisingly the cyclization precursor is not stable and decomposes when using too low concentrations $P_2O_5$ or in pure methanesulfonic acid.

The process Step A comprises the preparation of the cyclization precursor by condensation of the aniline with the 2-($R^2$-oxymethylene)propanedioate compound, which can be carried out at temperatures between 70 to 140° C., preferably 80 to 130° C., more preferably 90 to 120° C. The reaction is preferably carried out at 50 mbar to 1 atm. Preferably, in said step residual ethanol is removed to obtain an excellent chemoselectivity in the subsequent cyclization step.

The resulting cyclization precursor can either be used in the subsequent reaction in the form of a melt or diluted in an inert solvent. If a melt is used, a reaction temperature of at least 80° C. is required. Preferably, the intermediate condensate is used in diluted form. Dilution can be carried out in any suitable solvent, including e.g. toluene, chlorobenzene, xylene, anisole, mesitylene, 1,2-dichlorobenzene etc., or mixtures thereof. Preferred solvents are toluene, chlorobenzene and xylene, with toluene being most preferred.

Preferably toluene is selected as the inert solvent. Diluting the intermediate condensate, e.g. in toluene (up to 27 wt.-%), provides the advantage of a technically better feasible addition to the Eaton's reagent and the prevention of crystallisation thereof.

The concentrated Eaton's reagent is prepared separately, preferably at the same time while preparing the cyclization precursor.

Then, the cyclization precursor and the Eaton's reagent are combined for activating the cyclocondensation reaction. Therein, the cyclization precursor can be added to the Eaton's reagent or the other way round. It is preferred to add the cyclization precursor to the the prepared Eaton's reagent.

The subsequent cyclisation reaction can be carried out at a temperature between 30 to 110° C., preferably 60 to 100° C., more preferably 70 to 90° C.

The total amount of phosphorous pentoxide can be divided into two or more portions, preferably up to eight portions, and added batchwise.

The compound (I) can be isolated by partial neutralization of the acidic mother liquor, e.g. with soda lye, whereas the neutralization has to be controlled to avoid saponification of the product to the corresponding carboxylic acid.

The resulting filter cake can be washed and dried.

Process Step B-a:

In the process Step B-a of the process of the present invention a telescoped dehydroxyamination is carried out in a one-pot reaction without the necessity of isolating the unstable chloro-intermediate from the dehydroxychlorination. This could surprisingly be achieved by using stoichiometric amounts of thionyl chloride ($SOCl_2$).

Therein, for the first activating dehydroxychlorination step the thionyl chloride is dosed to the starting compound. Preferably, the thionyl chloride is dosed to the starting compound at a temperature between 80 to 110° C., preferably 85 to 105° C., more preferably 90 to 100° C. Under these reaction conditions, the reaction turned out to be particularly controllable and efficient.

Preferably thionyl chloride is added in amounts between 1.15 to 2.30 equivalents, preferably between 1.15 to 1.50 equivalents, more preferably between 1.15 to 1.30 equivalents.

The reaction is preferably carried out with catalytic amounts of N,N-dimethylformamide (DMF) or N,N-diethylformamide (DEF), N,N-di-n-butylformamide (DBF), N,N-diisopropylformamide (DIF), preferably with DEF, DBF or DIF, more preferably with DIF.

Preferred amount of catalyst are 0.8 to 5.0 mol %, more preferably 0.8 to 3.0 mol %, even more preferably 0.8 to 1.5 mol %.

Residual thionyl chloride and hydrogen chloride is distilled off and subsequently a desired amine is added to the reaction mixture, comprising the chloro-intermediate. The amine can be used in gaseous form or in an aqueous solution, the latter being preferred. It is particularly preferred to use dimethylamine. Therewith the dechloroamination of the chloro-intermediate can be performed by addition of the amine alone. Preferably, the amine compound, such as preferably dimethylamine, is added in an amount of $\geq 1.35$ equivalents, preferably 1.35 to 2.70 equivalents, more preferably 1.35 to 1.50 equivalents.

The addition of the amine compound, such as preferably of dimethylamine, is preferably carried out at temperatures between 20 to 60° C., preferably 30 to 50° C., more preferably at about 40° C.

The reaction can be carried out at 1.0 to 6.0 bar, preferably 1.0 to 3.0 bar, more preferably under atmospheric pressure.

Neutralization of the generated hydrochloric acid can be performed to reduce the minimum amount of amine needed.

Then, the pH should be controlled to be between about pH 8 to 10, preferably between about pH 9 to 10. In particular the pH should not exceed pH 10 to avoid regeneration of the compound (I) or ester saponification.

For the neutralization and pH adjustment it is possible to use common alkaline compounds such as sodium, potassium or lithium hydroxide solutions, or aqueous solutions of alkaline carbonates and alkaline earth metal carbonates. In principle any base being able to adjust and maintain a pH of 8 to 10, preferably 9 to 10 is suitable, provided the base is equal to or less nucleophilic as the amine compound used for the amination, such as e.g. dimethylamine or morpholine. Accordingly, it is also possible to use trialkylamines for adjusting the pH. Preferably an aqueous sodium hydroxide solution is used. It was in particular surprising that the new process step B-a does not require the use of dry amine compounds, e.g. dry dimethylamine, but can be carried out in an alkaline aqueous solution as described herein.

The resulting product can be isolated in pure form by extraction into aqueous hydrochloric acid and crystallization upon neutralization, e.g. with soda lye.

Process step B-a can be carried out using a suitable solvent such as toluene, chlorobenzene, xylene, mesitylene, 1,2-dichlorobenzene etc. Preferred solvents are toluene, chlorobenzene and xylene, with toluene being most preferred.

With this particular process Step B-a of the present invention it was surprisingly possible to eliminate one additional process step compared to the process as known from the unpublished international application PCT/EP2017/078319. It was in particular surprising, that therewith the reaction of a hydrolytic unstable intermediate in aqueous conditions became possible with excellent yield.

Process Step B-b:

In the process Step B-b of the process of the present invention a Suzuki-coupling is carried out using a suitable boron compound G and a palladium catalyst.

Suitable catalysts are in general all palladium catalyst which enable a Suzuki-coupling reaction. Examples are palladium(0)- and palladium(II) pre-catalysts such as $PdCl_2$, $Pd(OAc)_2$ (Ac=acetate), $Pd(NO_3)_2$, $Pd(acac)_2$ (acac=acetylacetonate), $Pd(dba)_2$ (dba=di-benzyliden-acetone) or palladium on a support such as activated carbon, without or in combination with a phosphine ligand L, and pre-formed palladium(0)- and palladium(II)-catalysts such as $PdCl_2(L)_2$ or $Pd(L)_4$.

Preferred are, $Pd(OAc)_2$, $Pd(acac)_2$ and $PdCl_2(L)_2$, without or in combination with a phosphine ligand. Most preferred is $Pd(acac)_2$ in combination with a phosphine ligand.

Suitable ligands L are in general all phosphine ligands which are known to give active palladium catalysts for a Suzuki-coupling reaction. Preferred are monodentate phosphine ligands $P(Ar)_n(Alkyl)_{3-n}$ with n=0, 1, 2 or 3, such as $PPh_3$, $P(o\text{-}Tolyl)_3$, $P(o\text{-}Anisyl)_3$, $P(p\text{-}Anisyl)_3$, $P(nBu)_3$, $P(tertBu)_3$, $P(Adamantyl)_2Ph$, $PPh_2(tertBu)$ or $PPh(tertBu)_2$. Preferred are $P(tertBu)_3$, $PPh_2(tertBu)$ and $PPh(tertBu)_2$. Most preferred is $P(tertBu)_3$.

It is possible to use the tetrafluoroborate salt for better handling of the highly air-sensitive free phosphine. However, it is also possible to use a solution of the free phosphine, e.g. in toluene, if all handling is done under an inert atmosphere, e.g. under argon.

The molar ratio of ligand L to palladium can vary in wide ranges. It is preferred to use a ratio of L/Pd between 0.5 and 10; more preferred is a ratio between 1 and 6.

In the process Step B-b a wide range of solvents can be used, such as toluene, xylenes, chlorobenzene, dichlorobenzenes, heptane, cyclohexane, methyl-cyclohexane, 1,4-dioxane, tetrahydrofuran, 2-methyl-tetrahydrofuran, 2,5-dimethyl-tetrahydrofuran, methyl-tertbutyl-ether, cyclopentyl-methyl-ether, methanol, ethanol, propanol, butanol, acetonitrile, butyronitrile, N,N-dimethylformamide, water, or mixtures of these solvents. Preferred are toluene, xylenes, chlorobenzene, methanol, ethanol, methyl-tertbutyl-ether, water, and mixtures of these solvents. Most preferred is a mixture of methyl-tertbutyl-ether and water.

In the process Step B-b a wide range of inorganic and organic bases can be used. Preferred are inorganic bases such as lithium hydroxide, sodium hydroxide, potassium hydroxide, calcium hydroxide, lithium carbonate, sodium carbonate, potassium carbonate, calcium carbonate, sodium fluoride and potassium fluoride. More preferred are sodium hydroxide, potassium hydroxide, sodium carbonate and potassium carbonate.

In the process Step B-b according to the present invention the boron compound G represents a boron compound of the general formula

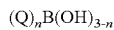

with
n=1, 2, or 3
or
G represents a boron compound of the general formula

with
M=lithium, sodium, or potassium,
or
G represents a boron compound of the general formula

with
M=lithium, sodium, or potassium,
or
G represents a boron compound of the general formula

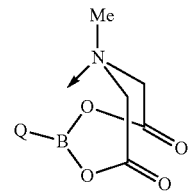

Therein, the boron compounds may be selected from suitable boronic acids, borinic acids, borates, borinates or MIDA-protected boronate esters (MIDA=N-methyliminodiacetic acid). Preferably, the boron compound G represents a boron compound, which is selected from (3,5-dichlorophenyl)boronic acid, bis(3,5-dichlorophenyl)borinic acid, tri(3,5-dichlorophenyl)boron; sodium tetra(3,5-dichloro-phenyl)borate, potassium (3,5-dichlorophenyl)trifluoroborate, or 2-(3,5-dichlorophenyl)-6-methyl-1,3,6,2-dioxazaborocane-4,8-dione (MIDA boronate). Most preferred are bis(3,5-dichlorophenyl)borinic acid and (3,5-dichlorophenyl)boronic acid.

In the process Step B-b a surprisingly low catalyst loading can be used to achieve high yields. Preferred are catalyst loadings between 0.1 and 1 mol %, referred to the starting material. More preferred are catalyst loadings between 0.2 and 0.8 mol %. Most preferred are catalyst loadings between 0.3 and 0.6 mol %.

The process Step B-b of the present invention should preferably be controlled so that the amount of residual palladium is reduced to ≤200 ppm, preferably <200 ppm, more preferably the amount of residual palladium is reduced to ≤100 ppm, most preferably <100 ppm. With the process Step B-b of the present invention it was surprisingly possible to achieve such low residual palladium amounts. If necessary, a further reduction can be achieved by applying a subsequent recrystallization step.

It is also possible, to further reduce the residual palladium by applying a subsequent extraction with an aqueous solution of acetylcystein. Therewith, an efficient depalladation can be achieved to prevent partial hydrodechlorination in a subsequent saponification step (e.g. Step B-c). Accordingly, this additional acetylcystein treatment is particularly suitable in the case of conducting process Step B-b prior to process Step B-c of the present invention.

It is possible to further reduce the residual palladium content by applying the acetylcystein treatment and/or the recrystallization step.

It further turned out, that surprisingly with the process Step B-b of the present invention it is also possible to achieve a reduction of PCB80 from >4000 ppm to <500 ppm.

Process Step B-c:

In the process Step B-c of the process of the present invention a saponification of the group [—(C=O)—O—$C_1$-$C_3$-alkyl] is carried out.

Therein, the saponification can be carried out by applying common saponification conditions. In particular, it is possible to use common hydroxide compounds such as alkali metal hydroxides and alkaline earth metal hydroxides, such as in particular sodium, potassium or lithium hydroxide. Preferably, sodium hydroxide is used.

Besides these bases, alkali metal carbonates and alkaline earth metal carbonates, such as in particular sodium, potassium, lithium, magnesium or calcium carbonate can be used.

The reaction is preferably carried out in a water/alcohol mixture at temperatures of 20-70° C. As alcohols, aliphatic alcohols can be used. Preferably, ethanol and methanol is used.

In the process Step B-c it is particularly preferred to use an ester compound as the starting compound, having a residual palladium content of ≤200 ppm, preferably ≤100 ppm. When using ester compounds as the starting compound with higher palladium levels in the saponification Step B-c, significant amounts of the hydrodechlorinated ester and hydrodechlorinated saponified carboxylic acid could occur.

Preferably, the saponification is carried out under intense stirring.

It is further preferred, that in Step B-c the saponified product is transferred and isolated as a salt, preferably as a HCl salt. It was found that compared to the free carboxylic acid form of the saponified product of Step B-c the salt exhibits increased stability when stored and applied in further reaction steps and exhibits less tendency of decomposing.

Process Step B-d:

In the process Step B-d of the process of the present invention a further coupling of the group A as defined supra is carried out.

Preferably, in Step B-d the starting compound is used in the form of the salt, preferably in the form of the HCl salt, as described in context with process Step B-c supra.

In the process Step B-d of the present invention 4-(4,6-dimethoxy-1,3,5-triazin-2-yl)-4-methyl-morpholinium chloride (DMT-MM) is used as the coupling agent. It surprisingly turned out that using DMT-MM for the coupling instead of e.g. TBTU (2-(1H-benzotriazole-1-yl)-1,1,3,3-tetramethylaminium tetrafluoroborate) or HATU (1-[bis(dimethylamino)methylen]-1H-1,2,3-triazolo[4,5-b]pyridinium 3-oxid hexafluorophosphat) as described in the unpublished international application PCT/EP2017/078319 is advantageous. In particular, using DMT-MM instead of HATU increases the yield significantly from 66% to 90%. Furthermore, DMT-MM as used in the process of the present invention, is far more cost effective and technically feasible.

The coupling reaction can be carried out by using the isolated coupling reagent DMT-MM. However, surprisingly it turned out, that the coupling reaction can also be carried out by preparing DMT-MM from 2-chloro-4,6-dimethoxy-1,3,5-triazine (CDMT) and N-methylmorpholine (NMM) in situ.

The concentration of the isolated coupling reagent CMT-MM must be higher due to the unfavourable energy potential of −1110 J/g at an onset temperature of 120° C., whereas the in situ preparation of DMT-MM allows a reduction of the amount of the accordingly prepared DMT-MM. In the process Step B-d of the the present invention it is thus particularly preferred to generated the coupling agent DMT-MM in situ from NMM and CDMT.

To prevent product crystallisation after addition of the compound A-$NH_2$ crystal crushing can be effected.

Process step B-d can be carried out using a suitable solvent such as toluene, chlorobenzene, anisole, tetrahydrofurane etc. Preferred solvents are toluene and chlorobenzene, with toluene being most preferred.

Preferably, the amount of the amine building block is 1.05 to 1.4 equivalents, preferably 1.1 to 1.3 equivalents, more preferably 1.1 to 1.2 equivalents.

Preferably, the amount of NMM is 5.0 to 15.0 equivalents, preferably 5.0 to 10.0 equivalents, more preferably 5.0 to 7.5 equivalents.

Preferably, the amount of CDMT is 1.25 to 2.00 equivalents, preferably 1.25 to 1.80 equivalents, more preferably 1.25 to 1.35 equivalents.

Preferably, the reaction is carried out at temperatures between 20 to 60° C., preferably 25 to 50° C., more preferably 30 to 40° C.

The isolation of the product from Step B-d is preferably carried out under reflux in tert-butylmethylether, which accelerates the stripping of the reaction solvents.

Further Aspects of the Process of the Present Invention:

The product resulting from the process according to the present invention can be subjected to further processing steps, including for example washing, purification, recrystallization and drying steps, which are commonly known to a skilled person.

The compounds and intermediates produced according to the process of the present invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or dichloromethane/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

The products (compounds and intermediates) resulting from the process according to the present invention can be converted to any salt, preferably pharmaceutically acceptable salts, by any method which is known to the person skilled in the art. Similarly, any salt of a compound or intermediate of the present invention can be converted into the free compound, by any method which is known to the person skilled in the art.

It is also possible to prepare isotopic variants of the compounds according to the present invention with the process described herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

With the process of the present invention it is possible to obtain the desired product in high yield and high purity.

It is further possible to provide the desired product in enantiomeric excess of >80%, preferably >85%, preferably >90%, more preferably >95%, or even up to 99%.

Further, it is possible to prepare the desired product having very low PCB80 contents of ≤1.0 ppm, preferably ≤0.5 ppm, more preferably ≤0.1 ppm and very low residual palladium contents of ≤20 ppm, preferably ≤10 ppm.

Definitions

In the context of the present invention the term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of the present invention, means "1, 2, 3, 4 or 5, particularly 1, 2, 3 or 4, more particularly 1, 2 or 3, even more particularly 1 or 2".

As used herein, the position via which a respective substituent is connected to the rest of the molecule may in a drawn structure be depicted by a hash sign (#) or a dashed line in said substituent.

The term "comprising" when used in the specification includes "consisting of".

If within the present text any item is referred to as "as mentioned herein" or "as described herein", it means that it may be mentioned or described anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_4$-alkyl" means a linear or branched, saturated, monovalent hydrocarbon group having 1, 2, 3 or 4 carbon atoms, e.g. a methyl, ethyl, n-propyl, isopropyl, n-butyl, sec-butyl, isobutyl or a tert-butyl group, or an isomer thereof. The term "$C_1$-$C_3$-alkyl" means a linear or branched, saturated, monovalent hydrocarbon group having 1, 2 or 3 carbon atoms, e.g. a methyl, ethyl, n-propyl or isopropyl group.

The term "$C_1$-$C_4$-halogenoalkyl" means a linear or branched, saturated, monovalent hydrocarbon group in which the term "$C_1$-$C_4$-alkyl" is as defined supra, and in which one or more of the hydrogen atoms are replaced, identically or differently, with a halogen atom. Particularly, said halogen atom is a fluorine atom. More particularly, all said halogen atoms are fluorine atoms ("$C_1$-$C_4$-fluoroalkyl"). Said $C_1$-$C_4$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

In general, and unless otherwise mentioned, the heteroaryl or heteroarylene groups include all possible isomeric forms thereof, e.g.: tautomers and positional isomers with respect to the point of linkage to the rest of the molecule.

The term "$C_1$-$C_4$", as used in the present text, e.g. in the context of the definition of "$C_1$-$C_4$-alkyl" or "$C_1$-$C_4$-halogenoalkyl", means an alkyl group having a finite number of carbon atoms of 1 to 4, i.e. 1, 2, 3 or 4 carbon atoms.

When a range of values is given, said range encompasses each value and sub-range within said range.

For example:

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_1$-$C_3$" encompasses $C_1$, $C_2$, $C_3$, $C_1$-$C_3$, $C_1$-$C_2$ and $C_2$-$C_3$;

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

An oxo substituent in the context of the invention means an oxygen atom, which is bound to a carbon atom via a double bond, such as e.g. forming a group [—(C═O)—].

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds and intermediates of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds and intermediates of the present invention to exist as tautomers. The present invention includes all possible tautomers of the compounds and intermediates of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds and intermediates of the present invention, such as metabolites, hydrates, solvates, prodrugs, salts, in particular pharmaceutically acceptable salts, and/or co-precipitates.

The compounds and intermediates of the present invention can exist as a hydrate, or as a solvate, wherein the compounds and intermediates of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds and intermediates of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compounds of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the compounds of the present invention to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds and intermediates of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Further Embodiments

In accordance with a third aspect, the present invention relates to the process for preparing a compound according to the formula (II) as described supra, wherein the process steps are carried out in the following order with the substituents having the specific meaning as defined herein:

Step B-a:

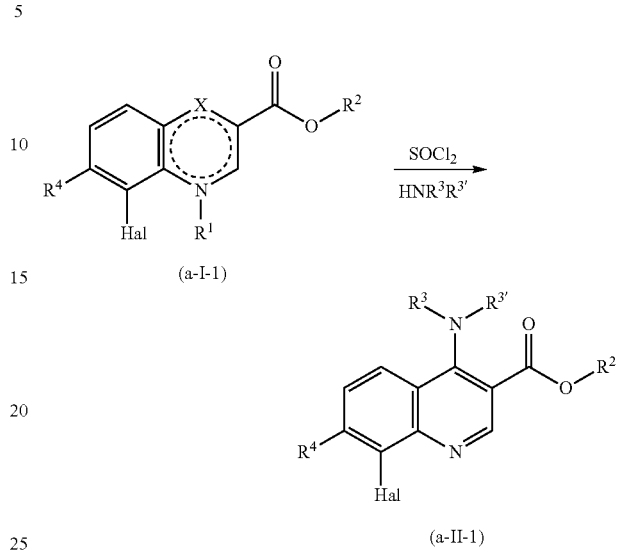

wherein $R^2$ is $C_1$-$C_3$-alkyl and $R^3$, $R^{3'}$ and $R^4$ have the meaning as defined supra; and wherein X is C=O and $R^1$ is hydrogen or X is C—OH and $R^1$ is absent, corresponding to the formulae (a-I-c) and (a-I-d):

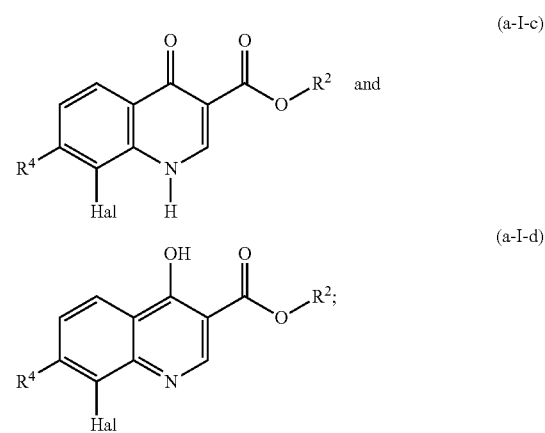

and wherein said process Step B-a is carried out using thionyl chloride ($SOCl_2$); followed by Step B-b:

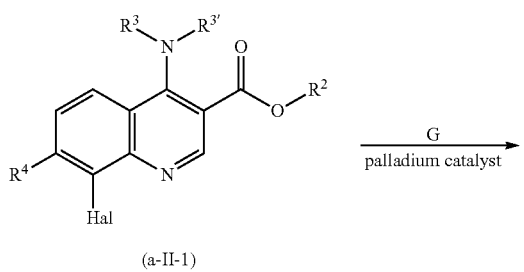

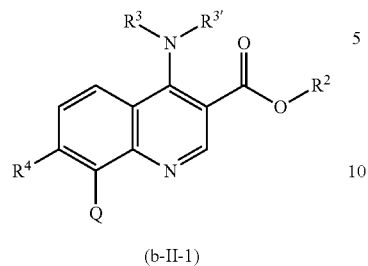

(b-II-1)

wherein G indicates a boron compound suitable for carrying out a Suzuki-reaction with G having the meanings as defined supra; followed by
Step B-c:

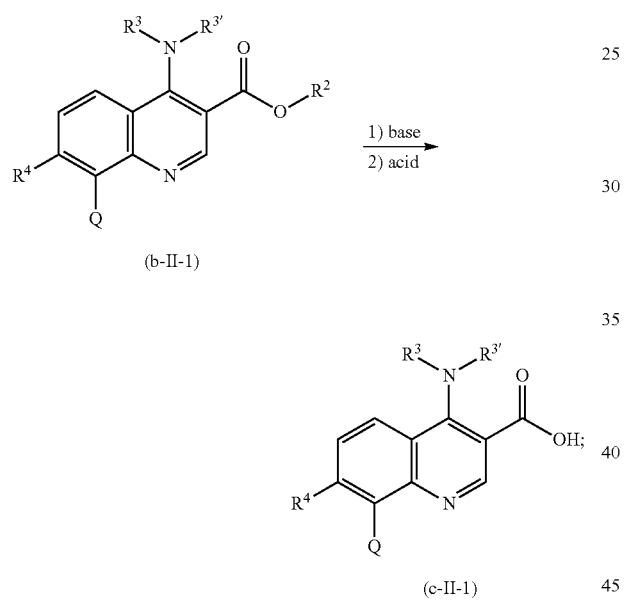

wherein base corresponds to for any alkali metal hydroxide and alkaline earth metal hydroxide as well as any alkali metal carbonate and alkaline earth metal carbonate; acid corresponds to any mineral acid; followed by
Step B-d:

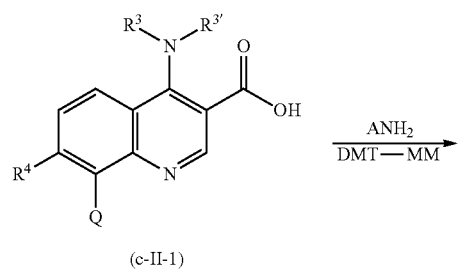

wherein A has the meaning as defined supra; and
wherein said process Step B-d is carried out by using DMT-MM as the coupling agent.

In accordance with a fourth aspect, the present invention relates to the process as described herein, wherein the process steps are carried out in the following order and represented by the following formulae:
Step B-a:

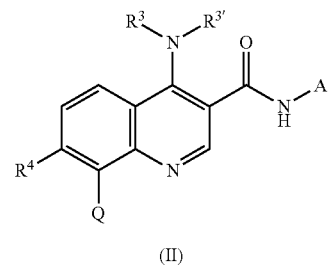

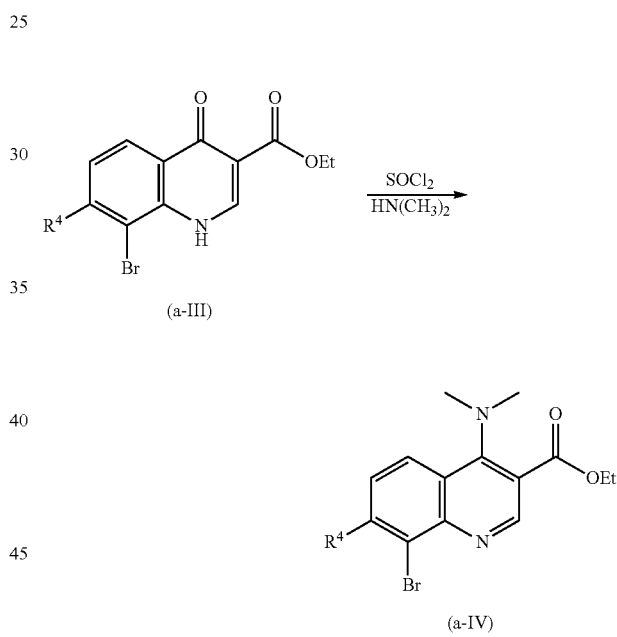

wherein $R^4$ has the meaning as defined supra, and wherein said process Step B-a is carried out using thionyl chloride (SOCl$_2$); followed by
Step B-b:

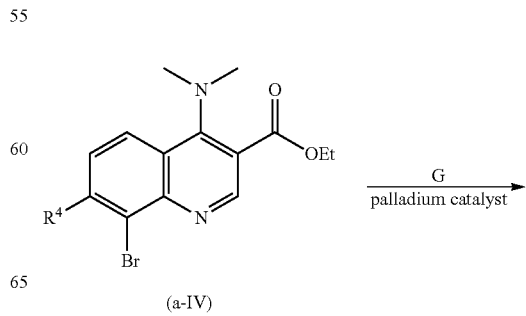

-continued

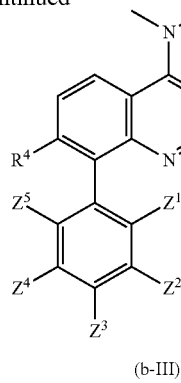

(b-III)

Wherein G indicates a boron compound suitable for carrying out a Suzuki-reaction with G having the meanings as defined supra, with Q being phenyl which may be substituted with 1 to 5 substituents $Z^1$ to $Z^5$, wherein $Z^1$ to $Z^5$ are independently selected from hydrogen, halogen, $C_1$-$C_4$-alkyl, and $C_1$-$C_4$-halogenoalkyl having 1-5 halogen atoms; followed by Step B-c:

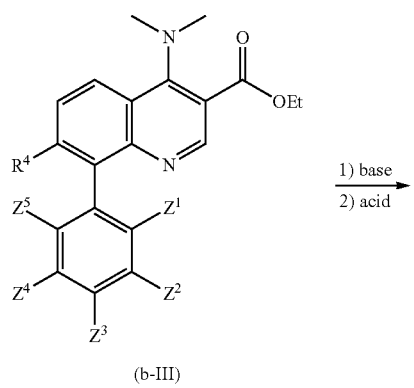

(b-III)

1) base
2) acid

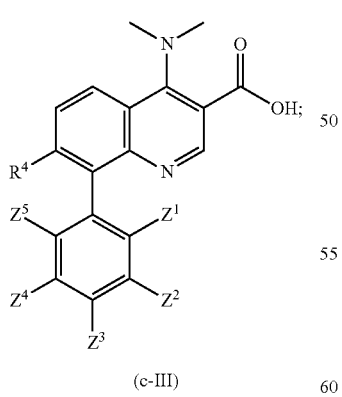

(c-III)

followed by wherein base corresponds to any alkali metal hydroxide and alkaline earth metal hydroxide, as well as any alkali metal carbonate and alkaline earth metal carbonate. Acid corresponds to any mineral acid.

Step B-d:

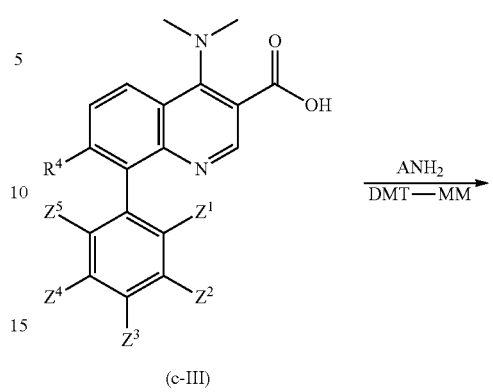

(c-III)

ANH₂
―――
DMT—MM

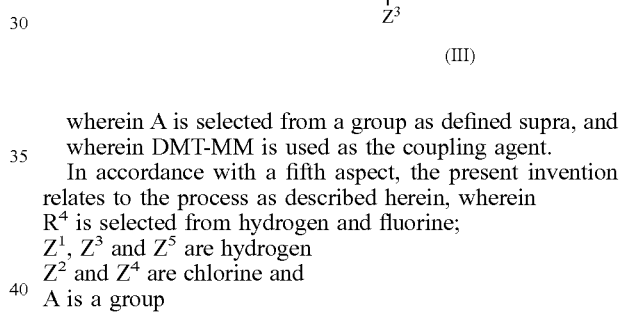

(III)

wherein A is selected from a group as defined supra, and wherein DMT-MM is used as the coupling agent.

In accordance with a fifth aspect, the present invention relates to the process as described herein, wherein
$R^4$ is selected from hydrogen and fluorine;
$Z^1$, $Z^3$ and $Z^5$ are hydrogen
$Z^2$ and $Z^4$ are chlorine and
A is a group

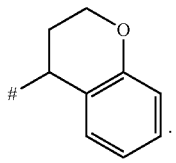

In accordance with a sixth aspect, the present invention relates to the process as described herein, wherein the group A is selected from the group consisting of

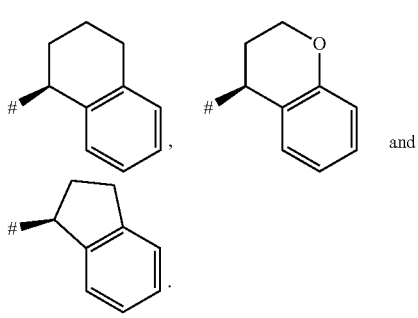

and

By using compounds with the group A as defined in the sixth aspect supra it is possible to obtain the compounds (and intermediates) of the present invention in the respective enantiomeric form, such as in particular the compound (II), (d-II) or (III) in the enantiomeric form

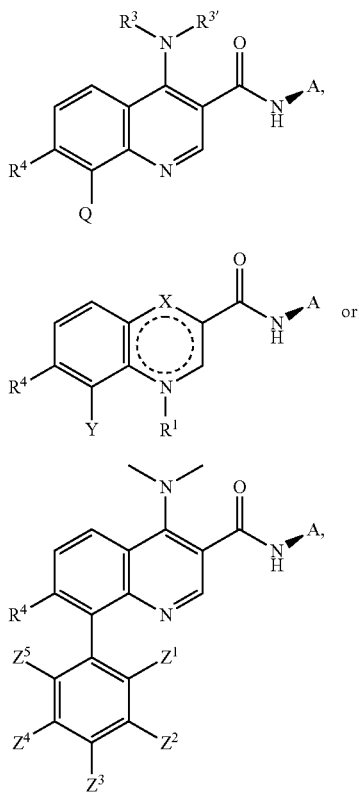

respectively.

In accordance with a seventh aspect, the present invention relates to the process as described herein, wherein one or more the process steps B-a, B-b, B-c and B-d is further characterized by one or more of the following process conditions:

Further Preferred Process Conditions in Step B-a:

Preferably, in Step B-a stoichiometric amounts of thionyl chloride are used.

Preferably, in Step B-a a pH of 8 to 10 is adjusted.

Further Preferred Process Conditions in Step B-b:

Preferably, in Step B-b the palladium-catalyst $Pd(acac)_2$ is used in an amount of ≥0.3 mol %.

Preferably, in Step B-b the amount of residual palladium is reduced to ≤200 ppm.

More preferably in Step B-b the amount of residual palladium is reduced to ≤100 ppm.

Preferably, in Step B-b a subsequent acetylcystein extraction and/or recrystallization step is carried out.

Further Preferred Process Conditions in Step B-c:

Preferably, in Step B-c the palladium content of the ester compound used as the starting compound is ≤200 ppm.

More preferably, in Step B-c the palladium content of the ester compound used as the starting compound is ≤100 ppm.

Preferably, in Step B-c the saponification of the ester compound is carried out by using NaOH.

Preferably, in Step B-c the sponified product is transferred and isolated as a salt.

More preferably the sponified product is transferred and isolated as a HCl salt.

Further Preferred Process Conditions in Step B-d:

Preferably, in Step B-d the starting compound is used in the form of the HCl salt.

Preferably, in Step B-d the coupling agent DMT-MM is generated in situ from NMM and CDMT.

In accordance with a further aspect, the present invention relates to the process as described herein, wherein the process Step A is further characterized by one or more of the following process conditions.

Further Preferred Process Conditions in Step A:

Preferably, in Step A the prepared intermediate cyclization precursor is used in the subsequent reaction diluted in an inert solvent.

More preferably, said intermediate cyclization precursor is used diluted in toluene.

Preferably, in Step A the total amount of the phosphorous pentoxide is added batchwise in two or more portions.

More preferably, the total amount of the phosphorous pentoxide is added batchwise in up to eight portions.

In accordance with a further aspect of the present invention, the process Step A is carried out represented by the following formulae:

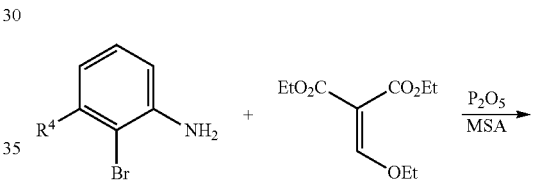

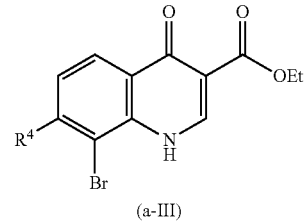

(a-III)

In accordance with an eighth aspect the present invention relates to the process as described anywhere herein for preparing compounds of the formulae

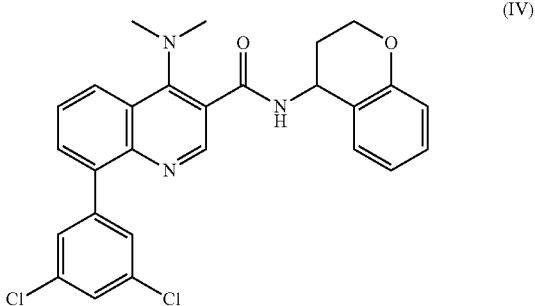

(IV)

-continued

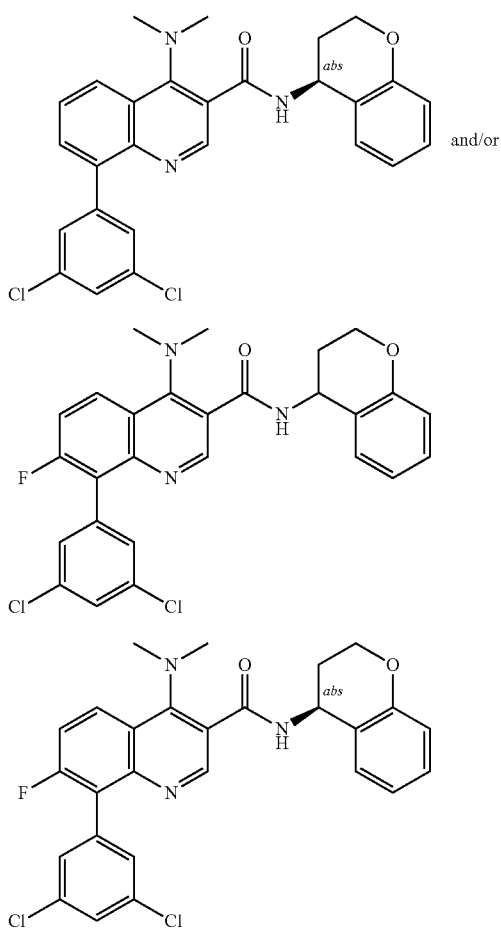

According to further aspects of the present invention it is possible to carry out the process as described herein with the following order of the process steps B-a, B-b, B-c and B-d, each as defined anywhere herein:

Process according to the present invention wherein the process steps are carried out in the order of starting with process Step B-b, followed by process Step B-a, followed by process Step B-c, followed by process Step B-d.

Process according to the present invention wherein the process steps are carried out in the order of starting with process Step B-b, followed by process Step B-c, followed by process Step B-d, followed by process Step B-a.

Process according to the present invention wherein the process steps are carried out in the order of starting with process Step B-b, followed by process Step B-c, followed by process Step B-a, followed by process Step B-d.

Process according to the present invention wherein the process steps are carried out in the order of starting with process Step B-c, followed by process Step B-d, followed by process Step B-a, followed by process Step B-b.

Process according to the present invention wherein the process steps are carried out in the order of starting with process Step B-c, followed by process Step B-d, followed by process Step B-b, followed by process Step B-a.

Process according to the present invention wherein the process steps are carried out in the order of starting with process Step B-c, followed by process Step B-a, followed by process Step B-b, followed by process Step B-d.

Process according to the present invention wherein the process steps are carried out in the order of starting with process Step B-c, followed by process Step B-a, followed by process Step B-d, followed by process Step B-b.

Process according to the present invention wherein the process steps are carried out in the order of starting with process Step B-c, followed by process Step B-b, followed by process Step B-a, followed by process Step B-d.

Process according to the present invention wherein the process steps are carried out in the order of starting with process Step B-c, followed by process Step B-b, followed by process Step B-d, followed by process Step B-a.

In accordance with a further aspect of the present invention, as mentioned above, process Step A as defined supra can be carried out prior to any of these alternative process orders supra. Additional process steps, comprising e.g. further washing, purification, recrystallisation drying, etc. as mentioned under "Further Aspects of the Process of the Present Invention" supra, may certainly be carried out likewise as described herein.

In accordance with an ninth aspect, the present invention relates to a process for preparing the intermediate compounds according to the formulae

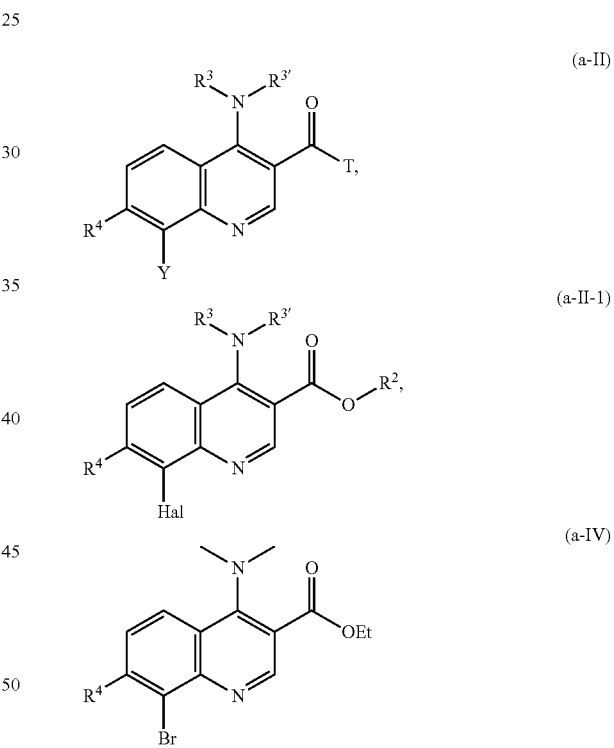

as defined supra and/or the intermediate compounds having the formulae

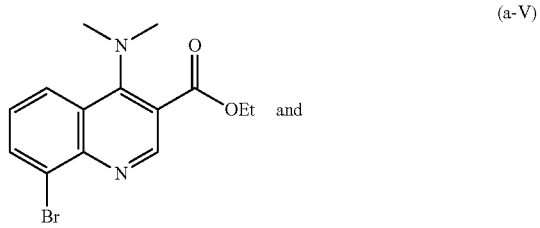

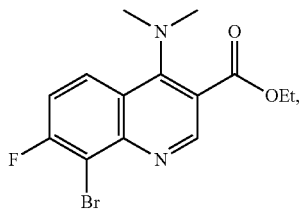
(a-VI)

by carrying out the process Step B-a as defined anywhere herein, followed by isolation and optionally purification of the resulting compounds. Therein, isolation in particular means recovery in solid form.

In accordance with a further aspect, the present invention relates to a process for preparing the intermediate compound according to the formula

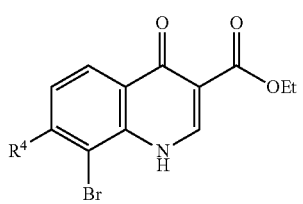
(a-III)

by carrying out the process Step A as defined anywhere herein, followed by isolation and optionally purification of the resulting compounds. Therein, isolation in particular means recovery in solid form.

In accordance with an tenth aspect, the present invention relates to a process for preparing the intermediate compounds according to the formulae

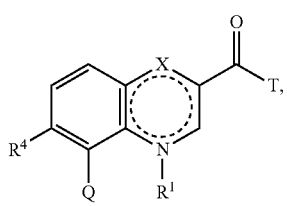
(b-II)

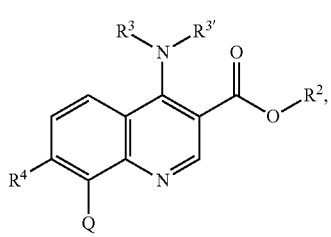
(b-II-1)

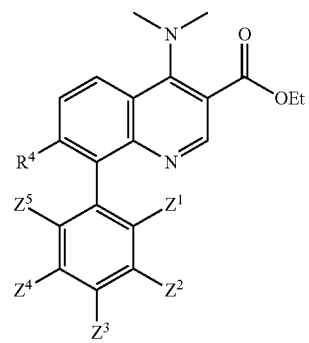
(b-III)

as defined supra and/or the intermediate compounds having the formulae

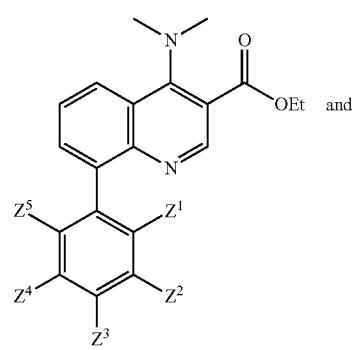
(b-IV)

and

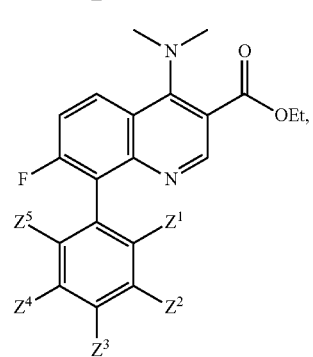
(b-V)

wherein $Z^1$ to $Z^5$ have the meaning as defined supra, by carrying out the process Step B-b as defined anywhere herein, followed by isolation and optionally purification of the resulting compounds. Therein, isolation in particular means recovery in solid form.

In accordance with a eleventh aspect, the present invention relates to a process for preparing the intermediate compounds according to the formulae

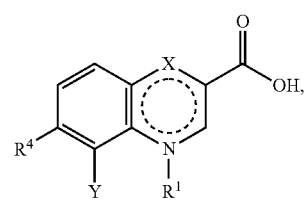
(c-II)

(c-II-1)

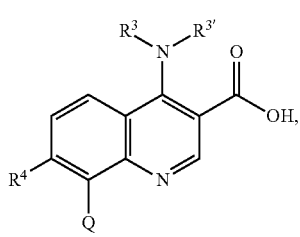

(c-III)

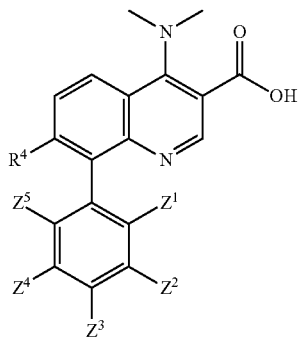

as defined supra and/or the intermediate compounds having the formulae (c-IV)

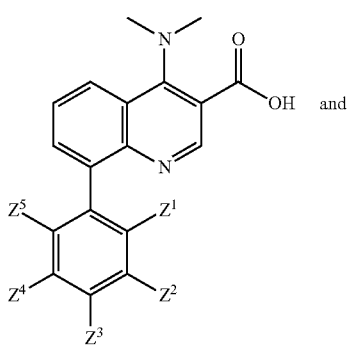 and (c-V)

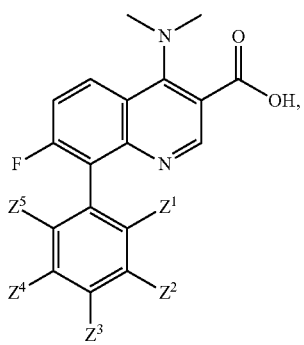

wherein $Z^1$ to $Z^5$ have the meaning as defined in any of the preceding claims,
by carrying out the process Step B-c as defined anywhere herein, followed by isolation and optionally purification of the resulting compounds. Therein, isolation in particular means recovery in solid form, preferably as a mineral acid salt, preferably as HCl salt.

In accordance with a twelfth aspect, the present invention relates to a process for preparing the intermediate compounds according to the formula (d-II)

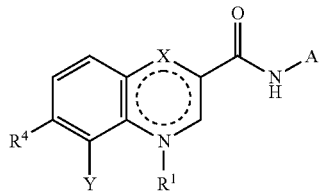

as defined supra by carrying out the process Step B-d as defined anywhere herein, followed by isolation and optionally purification of the resulting compounds. Therein, isolation in particular means recovery in solid form. It is clear for a skilled person that in said eleventh aspect the intermediate compound can only be achieved, if said Step B-d is not carried out as the final process step, which would result in the compounds of the formula (II) or (III) of the present invention.

In a particular embodiment of the ninth to twelfth aspect the intermediates are prepared by using compounds with the group A as defined in the sixth aspect supra, thus providing the respective intermediates as defined supra in the respective enantiomeric form.

In accordance with an thirteenth aspect, the present invention relates to the intermediate compounds according to any of the formulae (a-I-1), (a-II), (a-II-1), (a-III), (a-IV), (a-V), (a-VI), (b-II), (b-II-1), (b-III), (b-IV), (b-V), (c-II), (c-II-1), (c-III), (c-IV), (c-V) and (d-II) as defined supra or the respective enantiomeric form thereof (obtainable by using a compound with the group A as defined in the sixth aspect supra).

In accordance with an fourteenth aspect, the present invention relates to the use of the intermediate compounds as defined supra or as obtainable by a process as defined supra for preparing the compounds according to formula (II), (III), (IV) and/or (V) or the respective enantiomeric forms thereof (obtainable by using a compound with the group A as defined in the sixth aspect supra), such as in particular the compounds according to formula (IV') and/or (V') as defined supra.

In accordance with an fifteenth aspect, the present invention relates to the use of the intermediate compounds according to the formulae (a-I-1), (a-II), (a-II-1), (a-III), (a-IV), (a-V) and (a-VI) as defined supra or as obtainable by a process as defined supra for preparing the intermediate compounds according to the formulae (b-II), (b-II-1), (b-III), (b-IV), (b-V), (c-II), (c-II-1), (c-III), (c-IV), (c-V) and (d-II), each as defined supra, as well as the respective enantiomeric forms thereof (obtainable by using a compound with the group A as defined in the sixth aspect supra).

In accordance with an sixteenth aspect, the present invention relates to the use of the intermediate compounds according to the formulae (b-II), (b-II-1), (b-III), (b-IV) and (b-V) as defined supra or as obtainable by a process as defined supra for preparing the intermediate compounds according to the formulae (a-I-1), (a-II), (a-II-1), (a-III), (a-IV), (a-V), (a-VI) (c-II), (c-II-1), (c-III), (c-IV), (c-V) and (d-II), each as defined supra, as well as the respective enantiomeric forms thereof (obtainable by using a compound with the group A as defined in the sixth aspect supra).

In accordance with an seventeenth aspect, the present invention relates to the use of the intermediate compounds according to the formulae (c-II), (c-II-1), (c-III), (c-IV) and (c-V) as defined supra or as obtainable by a process as defined supra for preparing the intermediate compounds according to the formulae (a-I-1), (a-II), (a-II-1), (a-III), (a-IV), (a-V), (a-VI), (b-II), (b-II-1), (b-III), (b-IV), (b-V) and (d-II), each as defined supra, as well as the respective enantiomeric forms thereof (obtainable by using a compound with the group A as defined in the sixth aspect supra).

In accordance with an eighteenth aspect, the present invention relates to the use of the intermediate compounds according to the formula (d-II) as defined supra or as obtainable by a process as defined supra for preparing the intermediate compounds according to the formulae (a-I-l), (a-II), (a-II-1), (a-III), (a-IV), (a-V), (a-VI), (b-II), (b-II-1), (b-III), (b-IV), (b-V), (c-II), (c-II-1), (c-III), (c-IV) and (c-V), each as defined supra, as well as the respective enantiomeric forms thereof (obtainable by using a compound with the group A as defined in the sixth aspect supra).

EXPERIMENTAL SECTION

The various aspects of the invention described in this application are illustrated by the following examples which are not meant to limit the invention in any way.

Experimental Section—General Part

All reagents, for which the synthesis is not described in the experimental part, are either commercially available, or are known compounds or may be formed from known compounds by known methods by a person skilled in the art.

Example 1—Synthesis of N-[(4S)-chroman-4-yl]-8-(3,5-dichlorophenyl)-4-(dimethylamino)quinoline-3-carboxamide The target compound of Example 1 is a compound having the formula (IV'), which is prepared via five steps commencing with 2-bromoaniline and process Step A, followed by process steps B-a, B-b, B-c and B-d in this specific order:

Process Step A:

In the first step, 2-bromoaniline is condensed with diethyl 2-(ethoxymethylene)propanedioate (DEMP) to give ethyl 8-bromo-4-oxo-1H-quinoline-3-carboxylate in 90% yield (96 w % purity).

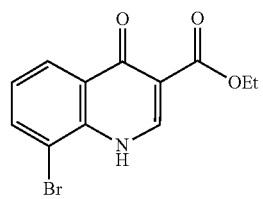 [SMILES: CCOC(=O)c1c[nH]c2c(Br)cccc2c1=O]

In a four-necked, round-bottomed flask A (4000 mL), equipped with a heatable dropping funnel, a reflux condenser, a mechanical stirrer and a thermometer, were placed 3.383 kg of methanesulfonic acid. The acid was heated to 125° C. internal temperature. To the acid was added 0.508 kg of phosphorus pentoxide. After full dissolution (1 hour) another portion of 0.508 kg of phosphorus pentoxide was dosed to the solution over 2 hours. During the dissolution process, another two-necked, round-bottomed flask B (1000 mL), equipped with a distillation head and a thermometer, was charged with 0.660 kg diethyl 2-(ethoxymethylene) propanedioate and 0.500 kg of 2-bromoaniline. The mixture was heated to 120° C. internal temperature under stirring and ethanol was distilled off over 4 hours until a HPLC measurement indicated full conversion to the cyclization precursor and 125 mL of ethanol were collected. Then the pressure was decreased to 70 mbar for removing residual 25 mL of ethanol from the mixture. Afterwards, the content of vessel B was filled into the dropping funnel of vessel A, which has been preheated to 100° C. jacket temperature. The precursor was then dosed into flask B over a period of 1 hour

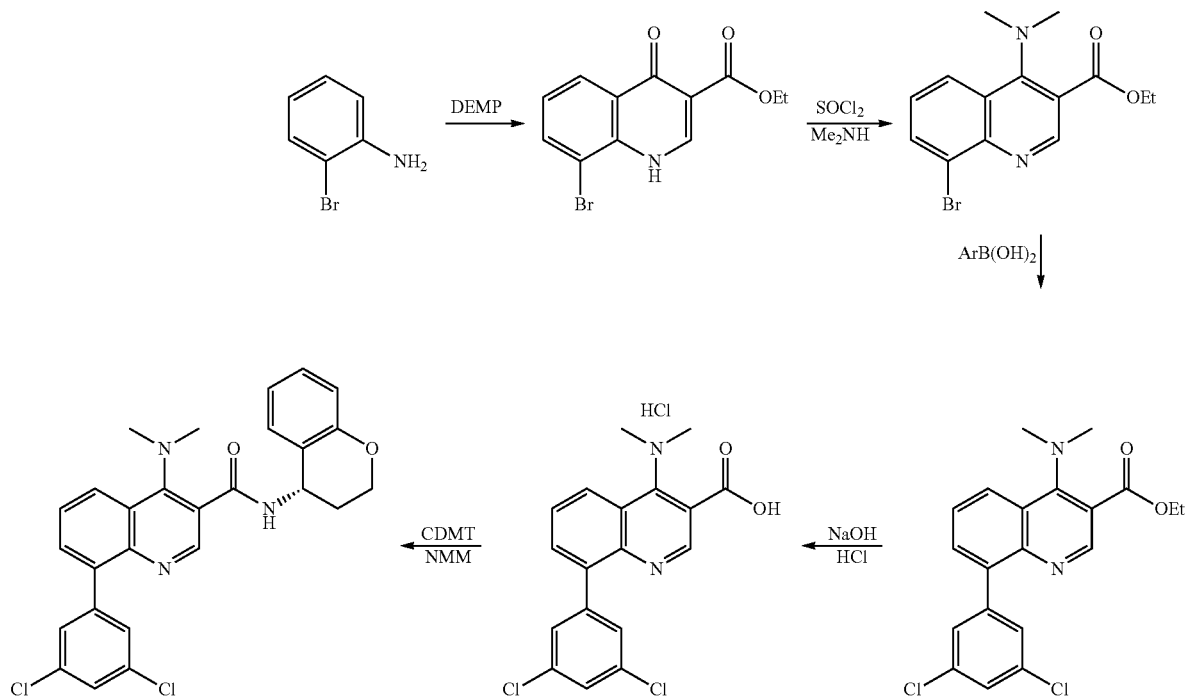

at 80° C. internal temperature. The resulting dark solution was stirred further for another hour until a HPLC measurement indicated full conversion. The dark solution was then added onto 7.500 kg of ice and the resulting slurry was stirred until a yellow suspension was obtained. To the suspension was added 3.524 kg of soda lye (33 w %) under stirring so that the internal temperature did not exceed 30° C. Afterwards the solid was filtered off and washed with 3.000 kg of deionized water until a pH neutral washing liquor was obtained. The solid was then washed with 1.950 kg of acetonitrile until the washing liqour lightened up to a yellowish colour. The yellow and sandy solid was then dried in vacuum.

As determined via Q-NMR-analysis, the remaining 0.792 kg solid contained 96 w % of ethyl 8-bromo-4-oxo-1H-quinoline-3-carboxylate, which corresponds to 0.760 kg pure product and a yield of 90%.

$^1$H-NMR (DMSO-d6, 400 MHz) δ (ppm)=11.62 (bs, 1H), 8.45 (d, J=8.0 Hz, 1H), 8.18 (d, J=8.0 Hz, 1H), 8.05 (d, J=8.0 Hz, 1H), 7.36 (dd, J=8.0, 8.0 Hz, 1H), 4.24 (q, J=7.0 Hz, 2H), 1.29 (t, J=7.0 Hz, 3H).

Process Step B-a:

Ethyl 8-bromo-4-oxo-1H-quinoline-3-carboxylate is subjected to dehydroxychlorination with thionylchloride and subsequent amidation with dimethylamine in the second step to yield ethyl 8-bromo-4-(dimethylamino)quinoline-3-carboxylate in 93% yield (96 w % purity) and in a telescoped fashion.

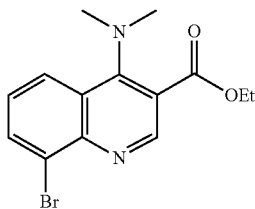 [SMILES: CCOC(=O)c1cnc2c(Br)cccc2c1N(C)C]

In a four-necked, round-bottomed flask (4000 mL), equipped with a dropping funnel, a reflux condenser with pressure equalizer, a mechanical stirrer and a thermometer, were placed 500.0 g of ethyl 8-bromo-4-oxo-1H-quinoline-3-carboxylate (purity: 96.7 w %) 1.65 g of N,N-diisopropylformamide and 1500.0 g of toluene. The suspension was heated to 100° C. internal temperature while being gently mixed. After having reached the temperature 223.4 g of thionyl chloride were dosed to the mixture over a period of 1.5 h. After the dosing was completed, the mixture was stirred for further 1.5 h until a HPLC measurement indicated full conversion to the chloro-substituted intermediate. Afterwards overall 250 mL of residual thionyl chloride, hydrogen chloride and some toluene were distilled off to obtain a well mixable dark solution, which was cooled to 40° C. internal temperature. The reflux condenser was replaced via a pH electrode. Then 248.4 g of dimethylamine (40 w % in water) were dosed to the solution within 30 minutes. The pH was adjusted with overall 365.0 g of soda lye (15 w %) to remain in the range of 9-10. The mixture was stirred for further 2.0 h at 40° C. until a HPLC measurement indicated full conversion. The mixture was then cooled to 25° C. and was then added to a mixture of 600 mL of toluene and 1000 mL of deionized water. After phase separation the organic phase was washed twice with each 600 mL of half-concentrated brine (13 w %). The combined aqueous phases were discarded. The organic phase was then extracted once with a mixture of 100 mL 20 w % aqueous hydrochloric acid and 400 mL deionized water and a second time with a mixture of 100 mL 20 w % aqueous hydrochloric acid and 200 mL deionized water. The organic phase was then discarded. Finally the combined aqueous phases were neutralized via addition of overall 640 g of 15 w % soda lye to reach pH=10 for complete product precipitation. The solid was filtered off and washed with overall 2500 mL of deionized water until the washing liquour was halide-free. The solid was dried in vacuum to receive a light yellow colour.

As determined via Q-NMR-analysis, the remaining 0.506 kg solid contained 96.6 w % of ethyl 8-bromo-4-(dimethylamino)quinoline-3-carboxylate, which corresponds to 0.489 kg pure product and a yield of 93%.

$^1$H-NMR (DMSO-d6, 600 MHz) δ (ppm)=8.83 (s, 1H), 8.22 (d, J=8.0 Hz, 1H), 8.15 (d, J=8.0 Hz, 1H), 7.50 (dd, J=8.0, 8.0 Hz, 1H), 4.40 (q, J=7.0 Hz, 2H), 3.06 (s, 6H), 1.37 (t, J=7.0 Hz, 3H).

Process Step B-b:

Ethyl 8-bromo-4-(dimethylamino)quinoline-3-carboxylate is then coupled with 3,5-dichlorophenylboronic acid in a Suzuki-reaction giving ethyl 8-(3,5-dichlorophenyl)-4-(dimethylamino)quinoline-3-carboxylate:

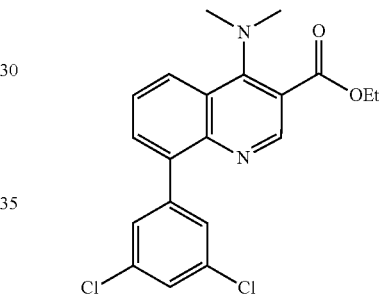

In a four-necked, round-bottomed flask (4000 mL), equipped with a reflux condenser with pressure equalizer, a mechanical stirrer and a thermometer, were placed in this order 167.9 g ethyl 8-bromo-4-(dimethylamino)quinoline-3-carboxylate (purity: 96.9), 2.375 kg MTBE (3.209 L), 0.687 kg H$_2$O, 139.2 g K$_2$CO$_3$ and 100 g 3,5-dichlorophenylboronic acid. The reaction mixture was purged with argon under stirring for 30 minutes. After that 0.920 g Pd(acac)$_2$ and 0.876 g HP(t-Bu)$_3$BF$_4$ were added. The reaction mixture was heated to 54° C. internal temperature (reflux) while being stirred under a gentle flush of argon. After 6 hours a HPLC measurement indicated full conversion. The mixture was cooled to 20° C. After phase separation and allocation of the pulp phase to the aqueous layer, the organic phase was dried over 15 g of MgSO$_4$ and the drying agent was filtered off. From the solution were distilled off 1.500 L of MTBE. To the solution was then added 425 mL of EtOH. The residual MTBE was distilled of at 70° C. under ambient pressure to leave a product solution in EtOH. The solution was gradually cooled to 22° C., leading to crystallization of the product. The solid was filtered and washed with 100 mL of ice-cold EtOH. Afterwards the yellow solid was dried in vacuum. Product content analysis via HPLC internal standard methodology of the combined mother and washing liquor revealed 24.79 g of ethyl 8-(3,5-dichlorophenyl)-4-(dimethylamino)quinoline-3-carboxylate in the filtrate, which corresponds to a yield of 13%.

As determined via Q-NMR-analysis, the remaining 0.165 kg solid contained 99 w % of ethyl 8-(3,5-dichlorophenyl)-4-(dimethylamino)quinoline-3-carboxylate, which corresponds to 0.163 kg pure product and a yield of 83%.

¹H-NMR (DMSO-d6, 600 MHz): δ=8.77 (s, 1H), 8.28 (dd, J=8.5; 1.4 Hz, 1H), 7.8 (dd, J=7; 1.4 Hz, 1H), 7.7 (dd, J=8.5; 7 Hz; 1H), 7.6 (m, 3H), 4.4 (q, J=7 Hz, 2H), 3.08 (s, 6H), 1.36 (t, J=7 Hz, 3H) ppm.

Process Step B-c:

This intermediate is saponified to 8-(3,5-dichlorophenyl)-4-(dimethylamino)quinoline-3-carboxylic acid hydrochloride:

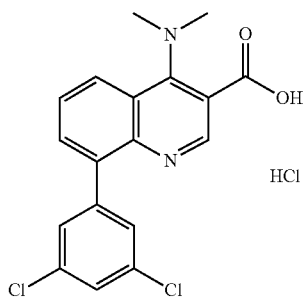 [SMILES: CN(C)c1c(C(=O)O)cnc2c(-c3cc(Cl)cc(Cl)c3)cccc12 ; Cl]

In a four-necked round-bottomed flask (500 mL), equipped with a mechanical stirrer, a dropping funnel and a thermometer, were placed 0.048 kg of ethyl 8-(3,5-dichlorophenyl)-4-(dimethylamino)quinoline-3-carboxylate (purity: 99 w %), 0.175 L of EtOH (138.3 g). The thick, yellowish suspension was heated to 50° C. internal temperature and was stirred with the mechanical stirrer. Within 1 h was added via dropping funnel 0.096 L of aqueous NaOH (10% in water). The mixture was stirred at 50° C. for 8 h until HPLC analysis revealed complete conversion.

After reaction completion 0.125 kg of volatiles were removed via distillation at 42° C. external heating and 80 mbar pressure. To the remaining residue of 0.158 g white suspension was added while stirring at 25° C. 0.080 L of deion. water. The suspension was cooled to 5° C. under stirring and the pH was adjusted to pH=1 via addition of 0.092 kg of HCl (20% in water). The solid was filtered off at 5° C. and washed with 0.050 L of ice-cold deion. water. Subsequently the solid was washed with 0.050 L of acetone. The filter cake was then dried under vacuum at 40° C. and the product was obtained as a white solid.

As determined via Q-NMR-analysis, the remaining 0.048 kg solid contained 95 w % of 8-(3,5-dichlorophenyl)-4-(dimethylamino)quinoline-3-carboxylic acid hydrochloride, which corresponds to 0.046 kg pure 8-(3,5-dichlorophenyl)-4-(dimethylamino)quinoline-3-carboxylic acid hydrochloride and a yield of 95%.

¹H-NMR (DMSO-d6, 400 MHz) δ (ppm)=8.57 (s, 1H), 8.42 (dd, J=8.5, 1.19 Hz, 1H), 7.87 (dd, J=7.23, 1.19 Hz, 1H), 7.78 (t, J=1.83 Hz, 1H), 7.7 (m, 1H), 7.63 (d, J=1.91 Hz, 2H), 3.44 (s, 6H).

Process Step B-d:

Finally, 8-(3,5-dichlorophenyl)-4-(dimethylamino)quinoline-3-carboxylic acid hydrochloride is amidated with (S)-Chromanamine.HCl via utilization of CDMT and NMM in 90% yield (>99 w % purity).

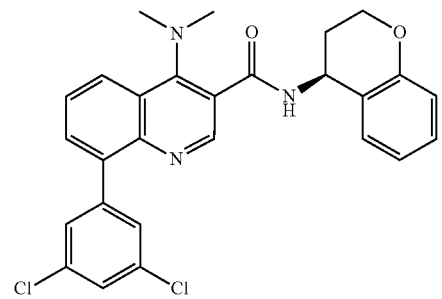 [SMILES: CN(C)c1c(C(=O)N[C@H]2CCOc3ccccc32)cnc2c(-c3cc(Cl)cc(Cl)c3)cccc12]

In a four-necked round-bottomed flask (500 mL), equipped with a mechanical stirrer, a dropping funnel and a thermometer, was added 20.0 g of 8-(3,5-dichlorophenyl)-4-(dimethylamino)quinoline-3-carboxylic acid hydrochloride (95 w %), 11.0 g CDMT and 160 mL of toluene. Via dosing of 25.0 g of NMM within 25 min the suspension was heated to 35° C. internal temperature and was maintained afterwards with external heating. The suspension turns yellow and becomes more viscous at the end of addition. However, the viscosity decreases subsequently under stirring. After 30 min stirring 10.4 g of (S)-Chroman-4-amine hydrochloride was added in one portion. Afterwards the suspension was stirred for another 8 hours until HPLC analysis indicated 99% conversion. After reaction completion, the reaction mixture was cooled down to room temperature (20-22° C.) and was transferred into a one-necked round-bottomed flask (1000 mL). Subsequently 320 mL of methylcyclohexane was added, the suspension was cooled to 0° C. and stirred at this temperature for 30 min. Then the solid was filtered through a glass frit (por. 3). The filter cake was washed with 100 mL of ice-cold acetonitrile, 100 mL of aqueous sodium hydroxide (5 w %) and 300 mL of deion. water. The solid was dried under vacuum (40° C., 70 mbar). Afterwards the complete amount of 24.2 g of dry solid were suspended in 120 mL of MTBE. Some crystals of the desired polymorph were added as seeds. Afterwards the suspension was stirred at 56° C. external heating for 4 hours. Finally, the suspension was cooled back to 22° C., the solid was filtered off and washed with 20 mL of MTBE. The product was then dried under vacuum (40° C., 50-10 mbar) for 2 hours. The product was obtained as a white solid.

As determined via Q-NMR and Q-HPLC analysis, the remaining 22.8 g solid contained 99.1 w % of (S)—N-(Chroman-4-yl)-8-(3,5-dichlorophenyl)-4-(dimethylamino)quinoline-3-carboxamide, which corresponds to 21.6 g pure product and a yield of 90%.

¹H-NMR (DMSO-d6, 400 MHz) δ (ppm)=9.10 (d, J=8.0 Hz), 8.63 (s, 1H), 8.24 (d, J=8.0 Hz, 1H), 7.80 (d, J=8.0 Hz, 1H), 7.67-7.63 (m, 4H), 7.37 (d, J=8.0 Hz, 1H), 7.17 (dd, J=8.0, 8.0 Hz, 1H), 6.94 (dd, J=8.0, 8.0 Hz, 1H), 6.80 (d, J=8.0 Hz, 1H), 5.79-5.72 (m, 1H), 4.21-4.32 (m, 2H), 3.07 (s, 6H), 2.25-2.15 (m, 1H), 2.09-2.00 (m, 1H).

In summary, the target compound (IV') can be produced in an overall yield of 59% over five steps commencing with 2-bromoaniline.

Example 2—Synthesis of N-[(4S)-chroman-4-yl]-8-(3,5-dichlorophenyl)-4-(dimethylamino)-7-fluoro-quinoline-3-carboxamide The target compound of Example 2 is a compound having the formula (V'), which is prepared in the same manner as described in Example 1 commencing with 2-bromo-3-fluoro-aniline in process Step A.

The invention claimed is:
1. A process for preparing a compound of formula (II) from a compound of formula (I):

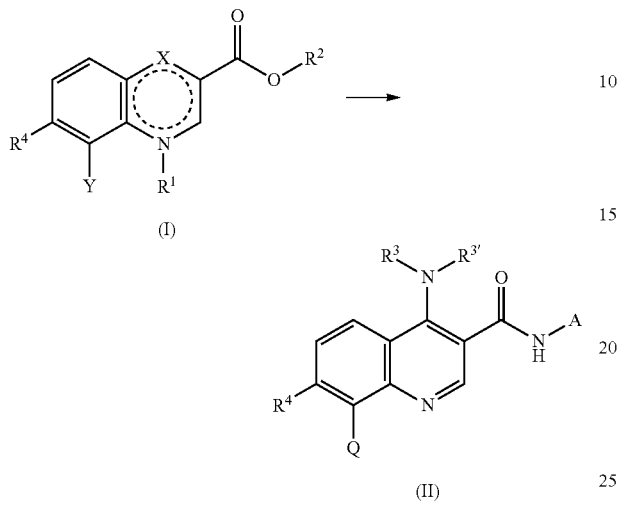

(I)

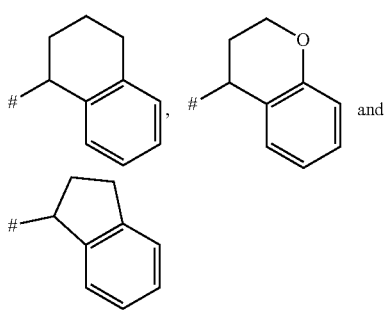

(II)

wherein
Y is halogen or Q;
X is C═O, C—OH, or C—NR³R³';

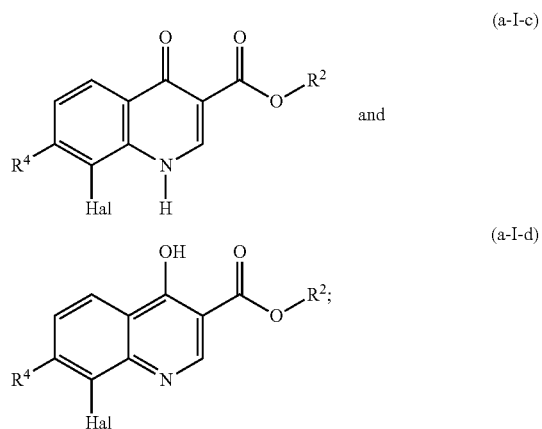

indicates an aromatic ring system or in the case that X is C═O valid double bonds in the ring system;
R¹ is absent in the case that X is C—OH or C—NR³R³', or is a hydrogen atom in the case that X is C═O;
R² is C₁-C₃-alkyl;
R³ and R³' independently of each other are hydrogen or C₁-C₃-alkyl, or
R³ and R³' together with the nitrogen to which they are bonded form a morpholinyl-ring;
R⁴ is hydrogen or halogen;
Q is phenyl, substituted with 1 to 5 substituents Z¹ to Z⁵, wherein
Z¹ to Z⁵ are independently from each other selected from the group consisting of hydrogen, halogen, C₁-C₄-alkyl, and C₁-C₄-halogenoalkyl having 1-5 halogen atoms; and
A is a group selected from the group consisting of

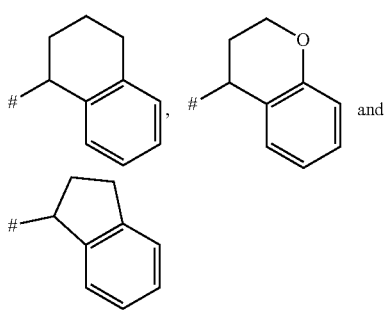

and wherein in the process the groups Q, NR³R³' and NH-A in formula (II) are obtained by reaction of the groups R², X and Y in formula (I) by the steps B-a, B-b, B-c and B-d, which are carried out in the following order:

Step B-a:

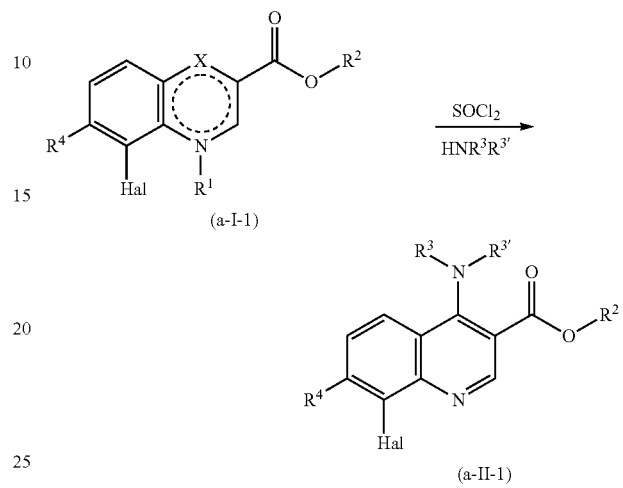

(a-I-1)

$\xrightarrow{\text{SOCl}_2}{\text{HNR}^3\text{R}^{3'}}$ (a-II-1)

wherein R² is C₁-C₃-alkyl and R³, R³' and R⁴ have the meaning as defined above, and wherein X is C═O and R¹ is hydrogen or X is C—OH and R¹ is absent, corresponding to the formulae (a-I-c) and (a-I-d):

(a-I-c)

and (a-I-d)

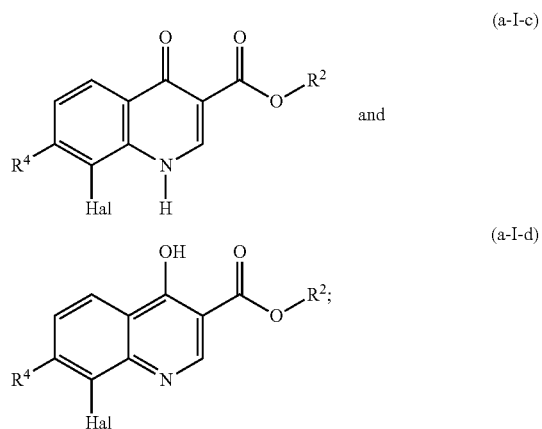

and wherein said process Step B-a is carried out using thionyl chloride (SOCl₂); followed by Step B-b:

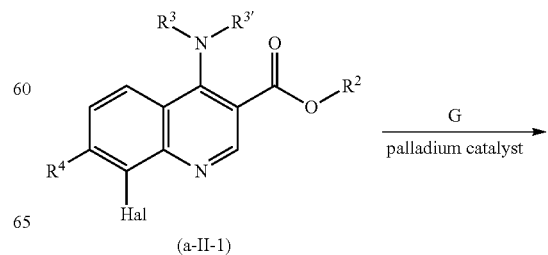

(a-II-1)

-continued

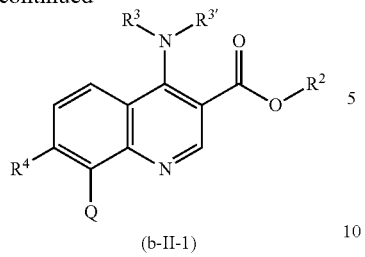

(b-II-1)

wherein G represents a boron compound of formula (Q)$_n$B(OH)$_{3-n}$ wherein
  n is 1, 2, or 3
or
G represents a boron compound of formula (Q)$_4$B$^-$M$^+$ wherein
  M is lithium, sodium, or potassium,
or
G represents a boron compound of formula

QBF$_3^-$M$^+$ wherein
  M is lithium, sodium, or potassium,
or
G represents a boron compound of formula
and wherein

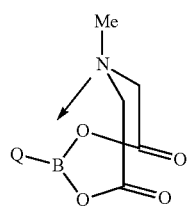

Q is phenyl, substituted with 1 to 5 substituents Z$^1$ to Z$^5$, wherein
Z$^1$ to Z$^5$ are independently from each other selected from the group consisting of hydrogen, halogen, C$_1$-C$_4$-alkyl, and C$_1$-C$_4$-halogenoalkyl having 1-5 halogen atoms; followed by
Step B-c:

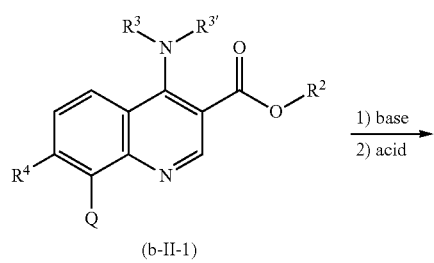

(b-II-1)

-continued

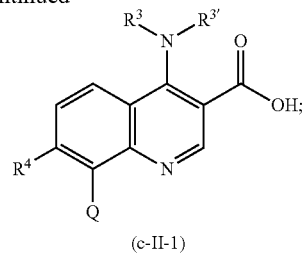

(c-II-1)

wherein R$^2$ is C$_1$-C$_3$-alkyl;
wherein base is an alkali metal hydroxide, an alkaline earth metal hydroxide, an alkali metal carbonate, or an alkaline earth metal carbonate;
wherein acid is a mineral acid; followed by
Step B-d:

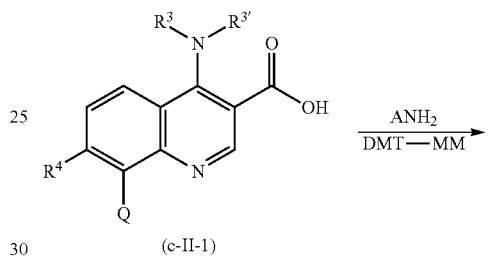

(c-II-1)

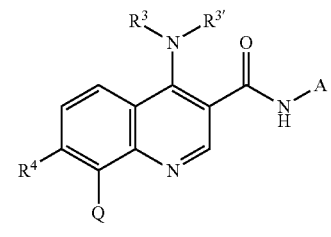

(II)

wherein A has the meaning as defined above; and
wherein said process Step B-d is carried out by using DMT-MM as the coupling agent;
and wherein in the reaction steps B-a to B-d the remaining substituents have the meaning as defined above.

2. The process according to claim 1, which further comprises the previous Step A for preparing the compound according to the formula (I):

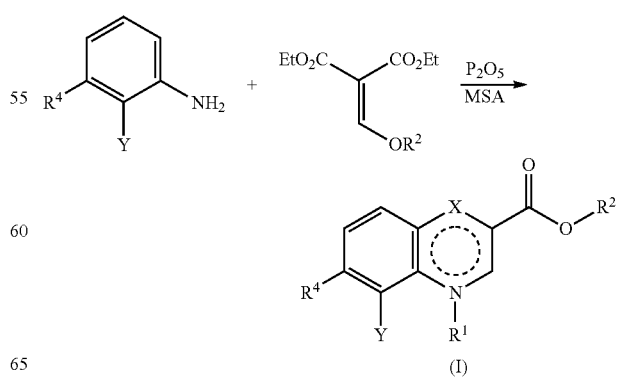

(I)

wherein P$_2$O$_5$ is present in the reaction batch in an absolute amount of >1 eq P$_2$O$_5$ and in an amount of 7.0 to 23.0 wt.-% relative to methane sulfonic acid (MSA).

3. The process according to claim 1, which is represented by the following formulae:

Step B-a:

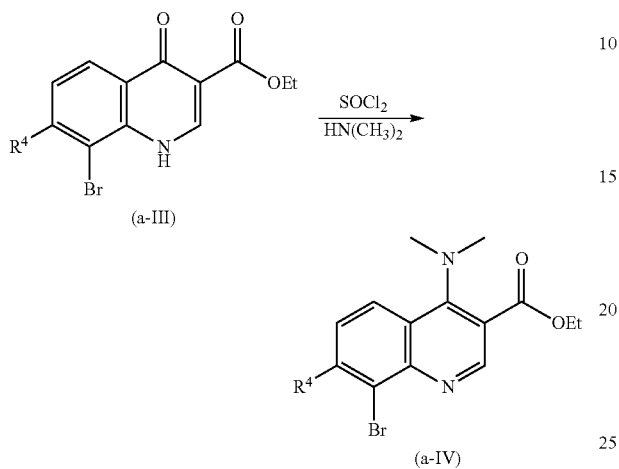

(a-III)

(a-IV)

wherein said process Step B-a is carried out using thionyl chloride (SOCl$_2$); followed by Step B-b:

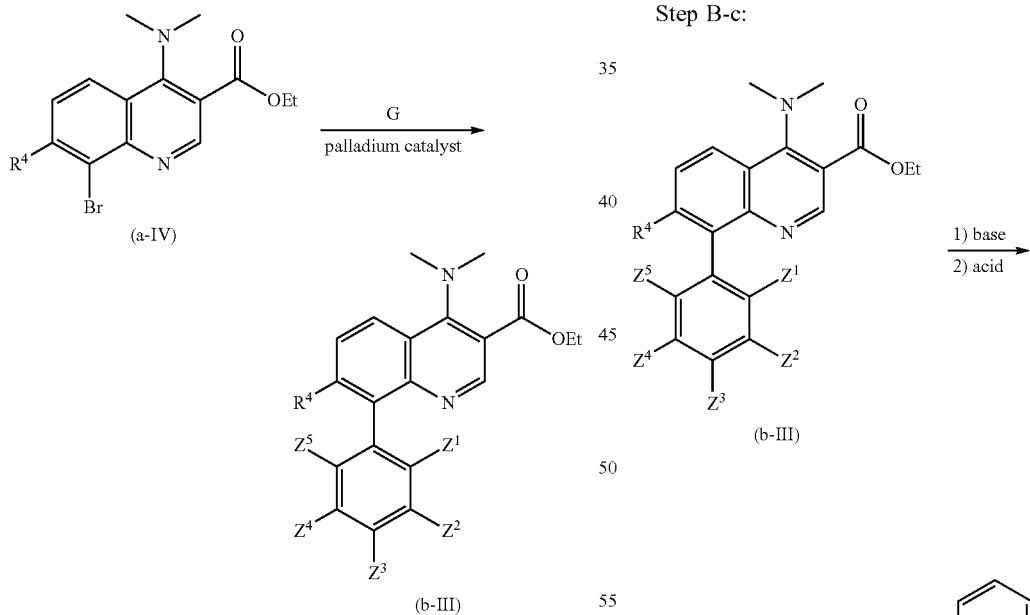

(a-IV)

(b-III)

wherein G represents a boron compound of formula (Q)$_n$B(OH)$_{3-n}$ wherein
  n is 1, 2, or 3
or
G represents a boron compound of formula (Q)$_4$B$^-$M$^+$ wherein
  M is lithium, sodium, or potassium,
or
G represents a boron compound of formula

QBF$_3^-$M$^+$ wherein
  M is lithium, sodium, or potassium,
or
G represents a boron compound of formula

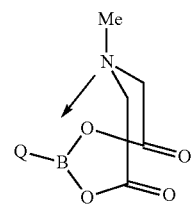

and wherein

Q is phenyl, substituted with 1 to 5 substituents Z$^1$ to Z$^5$, wherein

Z$^1$ to Z$^5$ are independently from each other selected from the group consisting of hydrogen, halogen, C$_1$-C$_4$-alkyl, and C$_1$-C$_4$-halogenoalkyl having 1-5 halogen atoms; followed by Step B-c:

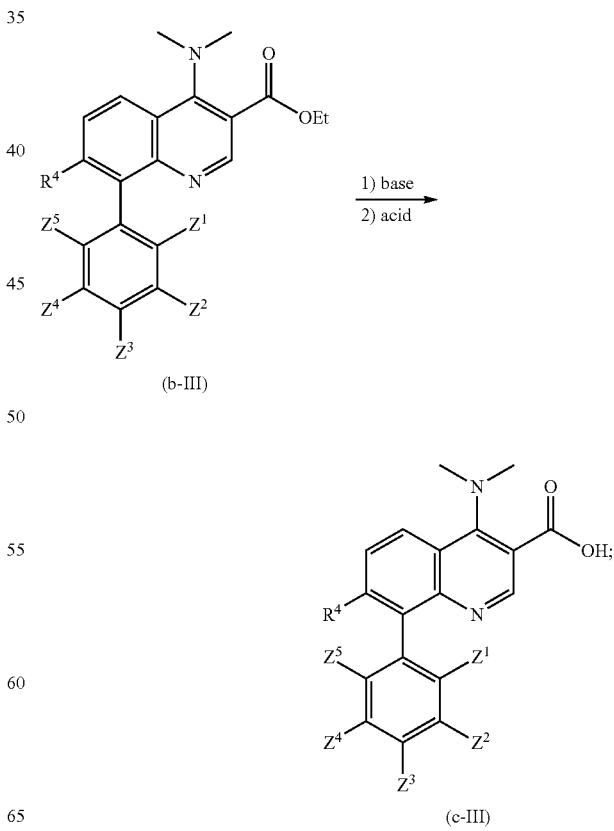

(b-III)

(c-III)

wherein R² is C₁-C₃-alkyl; wherein base is an alkali metal hydroxide, an alkaline earth metal hydroxide, an alkali metal carbonate, or an alkaline earth metal carbonate;

wherein acid is a mineral acid; followed by

Step B-d:

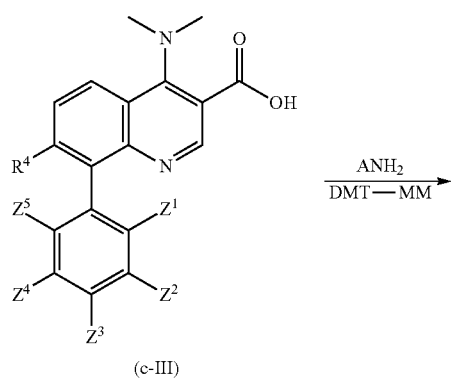

(c-III)

$\xrightarrow{\text{ANH}_2}{\text{DMT—MM}}$

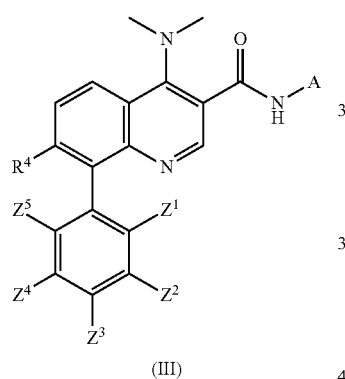

(III)

wherein A is a group selected from the group consisting of

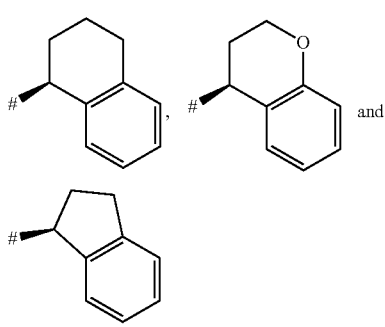

and wherein said process Step B-d is carried out by using DMT-MM as the coupling agent.

4. The process according to claim 3, wherein
R⁴ is selected from hydrogen and fluorine;
Z¹, Z³ and Z⁵ are hydrogen Z² and Z⁴ are chlorine and
A is a group

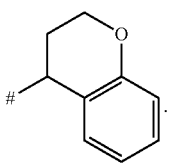

5. The process according to claim 1, wherein the group A is selected from the group consisting of

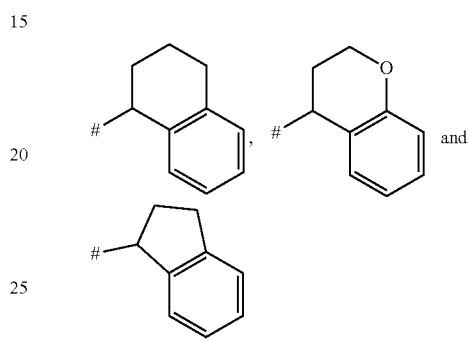
and thereby providing the compound (II) or (III) in the enantiomeric form

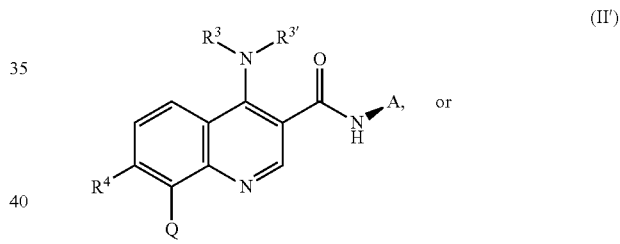

(II')

or

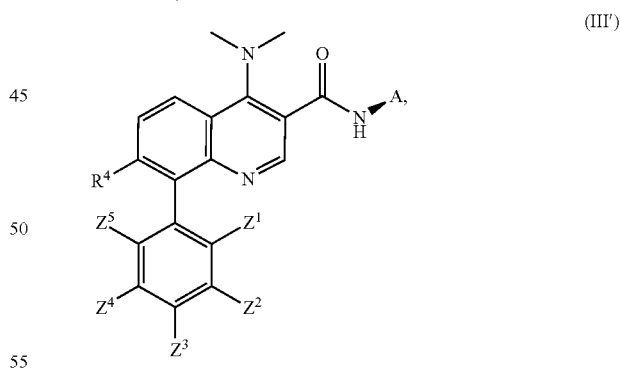

(III')

respectively.

6. The process according to claim 1, wherein one or more the process steps B-a, B-b, B-c and B-d is further characterized by one or more of the following process conditions:
in Step B-a stoichiometric amounts of thionyl chloride are used;
in Step B-a the amount of thionyl chloride is between 1.15 to 2.30 equivalents;
in Step B-a a pH of 8 to 10 is adjusted;
in Step B-a a solvent is used which is selected from the group consisting of toluene, chlorobenzene or xylene;

in Step B-a catalyst selected from the group consisting of DMF, DEF, DBF or DIF;
in Step B-a a catalyst is used in amounts between 0.8 to 5.0 mol %;
in Step B-a the amine compound is dimethylamine;
in Step B-a the amine compound is added in an amount of ≥1.35 equivalents;
in Step B-b the palladium-catalyst is used in an amount of ≥0.3 mol;
in Step B-b the amount of residual palladium is reduced to ≤200 ppm;
in Step B-b the palladium-catalyst is selected from the group consisting of, Pd(OAc)$_2$, Pd(acac)$_2$ and PdCl$_2$(L)$_2$, without or in combination with a phosphine ligand L;
in Step B-b, when present, the phosphine ligand L is a monodentate phosphine ligand P(Ar)$_n$(Alkyl)$_{3-n}$ with n=0, 1, 2 or 3;
in Step B-c the palladium content of the ester compound is ≤200 ppm;
in Step B-c the saponification of the ester compound is carried out by using NaOH;
in Step B-c the HCl salt of the resulting product is prepared;
in Step B-d the starting compound is used in the form of the HCl salt;
in Step B-d a solvent is used which is selected from the group consisting of toluene or chlorobenzene;
in Step B-d the coupling agent DMT-MM is used as the isolated DMT-MM compound or is generated in situ from NMM and CDMT;
in Step B-d the starting compound is used in an amount between 1.05 to 1.4 equivalents;
in Step B-d an amount of 5.0 to 15.0 equivalents;
in Step B-d and amount of 1.25 to 2.00 equivalents;
in Step A the prepared intermediate cyclization precursor is used in the subsequent reaction diluted in an inert solvent;
in Step A an absolute amount between 1.5 and 3.5 equivalents;
in Step A the amount of P$_2$O$_5$ relative to the amount of MSA is 7.0 to 23.0 wt. %; and
in Step A the total amount of the phosphorous pentoxide is added batchwise in two or more portions.

7. The process according to claim 1, wherein the compound of formula (II) is a compound of formula (IV), (IV'), (V) and/or (V'):

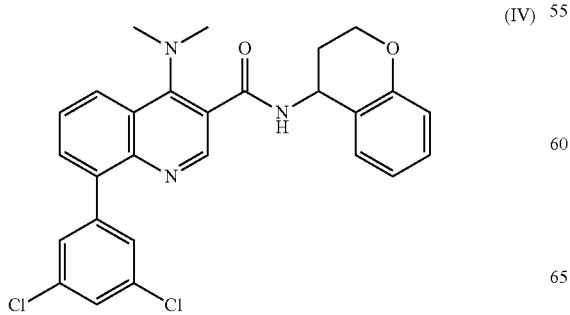
(IV)

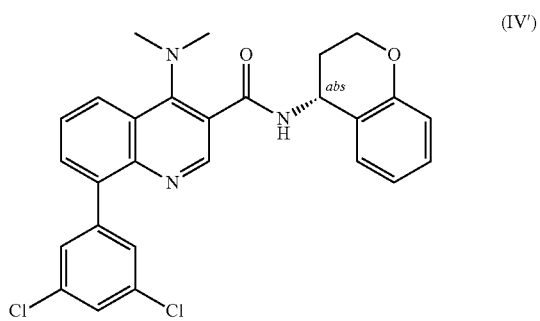
(IV')

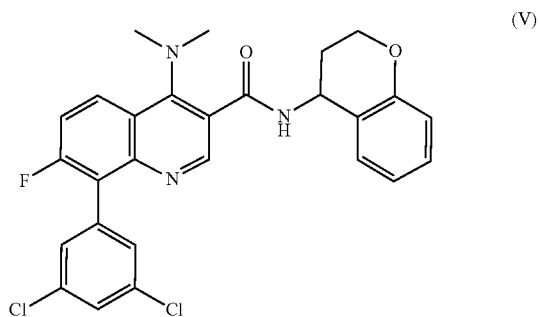
(V)

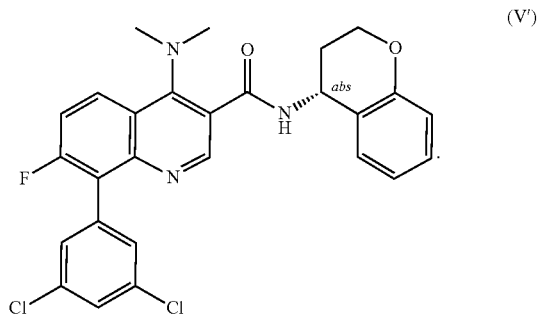
(V')

8. The process for preparing the intermediate compounds according to the formula (a-II-1) as defined in claim 1 and the intermediate compounds

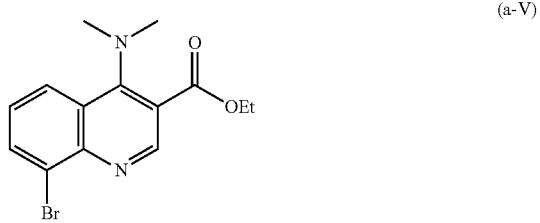 [SMILES: CCOC(=O)c1cnc2c(Br)cccc2c1N(C)C]
(a-V)

by carrying out the process Step B-a, followed by isolation and optionally purification of the resulting compounds.

9. The process for preparing the intermediate compounds according to the formula (b-III) as defined in claim 3 and the intermediate compounds

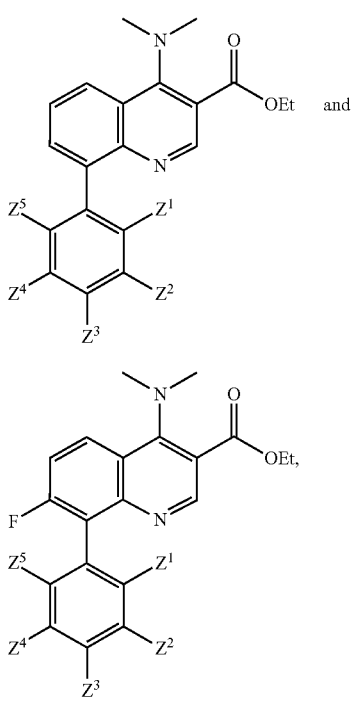

(b-IV)

(b-V)

wherein $Z^1$ to $Z^5$ are as defined in claim 1,
by carrying out the process Step B-b, followed by isolation and optionally purification of the resulting compounds.

10. The process for preparing the intermediate compounds according to the formula (c-II-1) as defined in claim 1 and the intermediate compounds

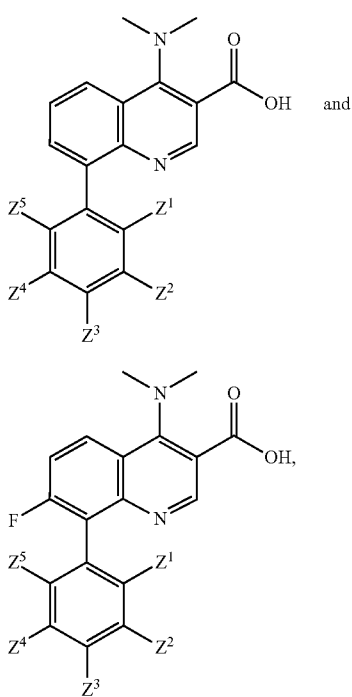

(c-IV)

(c-V)

wherein $Z^1$ to $Z^5$ are as defined in claim 1,
by carrying out the process Step B-c
followed by isolation and optionally purification of the resulting compounds.

11. The process for preparing the intermediate compounds according to the formula (a-IV) as defined in claim 3 and the intermediate compounds

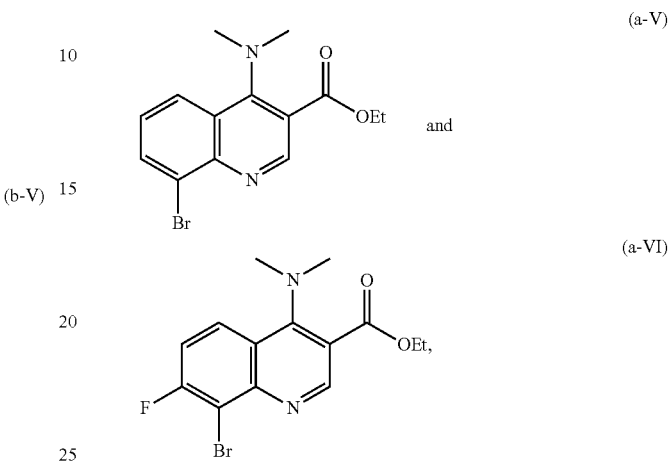

(a-V)

(a-VI)

by carrying out the process Step B-a, followed by isolation and optionally purification of the resulting compounds.

12. The process for preparing the intermediate compounds according to the formula (c-III) as defined in claim 3 and the intermediate compounds

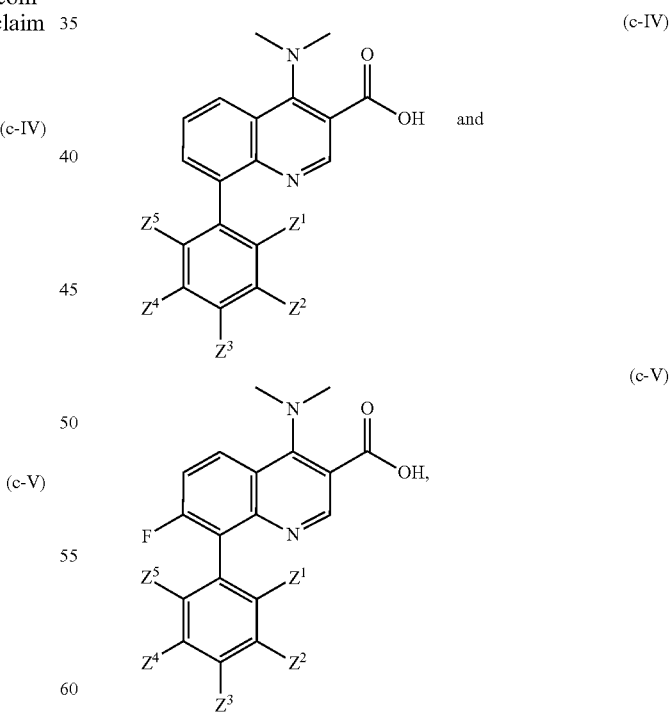

(c-IV)

(c-V)

by carrying out the process Step B-c
followed by isolation and optionally purification of the resulting compounds.

* * * * *